United States Patent
Galili et al.

(10) Patent No.: US 9,909,135 B2
(45) Date of Patent: Mar. 6, 2018

(54) TRANSGENIC PLANTS HAVING ALTERED DAHP SYNTHASE ACTIVITY

(75) Inventors: Gad Galili, Rehovot (IL); Asaph Aharoni, Rehovot (IL); Vered Tzin, Rehovot (IL); Sergey Malitsky, Rehovot (IL); Ilana Rogachev, Rehovot (IL)

(73) Assignee: Yeda Research and Development Co. Ltd., Rehovet (IL)

( * ) Notice: Subject to any disclaimer, the term of this patent is extended or adjusted under 35 U.S.C. 154(b) by 355 days.

(21) Appl. No.: 13/808,530

(22) PCT Filed: Jul. 6, 2011

(86) PCT No.: PCT/IL2011/000535
§ 371 (c)(1),
(2), (4) Date: Jan. 4, 2013

(87) PCT Pub. No.: WO2012/004795
PCT Pub. Date: Jan. 12, 2012

(65) Prior Publication Data
US 2013/0111631 A1    May 2, 2013

Related U.S. Application Data

(60) Provisional application No. 61/361,549, filed on Jul. 6, 2010.

(51) Int. Cl.
| | |
|---|---|
| C12N 15/82 | (2006.01) |
| C12N 9/02 | (2006.01) |
| A01H 5/10 | (2006.01) |
| C12N 9/88 | (2006.01) |
| C12N 9/10 | (2006.01) |

(52) U.S. Cl.
CPC ....... *C12N 15/8251* (2013.01); *C12N 9/1085* (2013.01); *C12N 9/88* (2013.01); *C12N 15/8243* (2013.01); *C12N 15/8254* (2013.01); *C12N 15/8255* (2013.01); *C12Y 205/01054* (2013.01)

(58) Field of Classification Search
CPC .................................................. C12N 15/8251
See application file for complete search history.

(56) References Cited

U.S. PATENT DOCUMENTS

| | | | | |
|---|---|---|---|---|
| 5,545,545 | A * | 8/1996 | Gengenbach | C12N 9/88 |
| | | | | 435/412 |
| 5,776,736 | A | 7/1998 | Frost | |
| 5,906,925 | A | 5/1999 | Liao | |
| 6,911,331 | B2 | 6/2005 | Famodu | |
| 7,790,431 | B2 | 9/2010 | Frost | |
| 2007/0118916 | A1* | 5/2007 | Puzio | C12N 15/8214 |
| | | | | 800/278 |
| 2008/0127368 | A1 | 5/2008 | Haring | |

FOREIGN PATENT DOCUMENTS

| | | |
|---|---|---|
| EP | 1270721 | 1/2003 |
| WO | 95/33843 | 12/1995 |
| WO | 00/05386 | 2/2000 |
| WO | 2006/021558 | 3/2006 |
| WO | 2009/072118 | 6/2009 |

OTHER PUBLICATIONS

Tzin, Vered, et al. "Expression of a bacterial feedback-insensitive 3-deoxy-d-arabino-heptulosonate 7-phosphate synthase of the shikimate pathway in Arabidopsis elucidates potential metabolic bottlenecks between primary and secondary metabolism." New Phytologist 194.2 (2012): 430-439.*
Maeda, H., and Dudareva N., "The shikimate pathway and aromatic amino acid biosynthesis in plants." Annual review of plant biology 63 (2012): 73-105.*
Hu, Changyun, et al. "Mutation analysis of the feedback inhibition site of phenylalanine- sensitive 3- deoxy- D- arabino-heptulosonate 7- phosphate synthase of *Escherichia coli*." Journal of basic microbiology 43.5 (2003): 399-406.*
Hu, Changyun, et al. "Mutation analysis of the feedback inhibition site of phenylalanine-sensitive 3-deoxy-D-arabino-heptulosonate 7-phosphate synthase of *Escherichia coli*." Journal of basic microbiology 43.5 (2003): 399-406.*
Purves, William K., et al. Life: The Science of Biology: vol. III: Plants and Animals. vol. 3. Macmillan, 2003; Chapter 9.*
Pribat, Anne, et al. "Nonflowering plants possess a unique folate-dependent phenylalanine hydroxylase that is localized in chloroplasts." The Plant Cell 22.10 (2010): 3410-3422.*
Tohge, Takayuki, et al. "Shikimate and phenylalanine biosynthesis in the green lineage." Frontiers in plant science 4 (2013): 62. 2013.*
Hu, C., et al., J. Basic Microbiol. 43(5):399-406.*
Hu, C., et al., 2003, J. Basic Microbiol. 43(5):399-406.*
Communication Pursuant to Article 94(3) EPC dated Sep. 29, 2014 From the European Patent Office Re. Application No. 11741693.3.
Aharoni, Asaph Galili, Gad (2011) Metabolic engineering of the plant primary-secondary metabolism interface. Curr Opin Biotechnol 22(2):239-244.
Brown, K. D. (1968) Regulation of Aromatic Amino Acid Biosynthesis in *Escherichia coli* K12. Genetics 60 (1):31-48.
Chomczynski, Piotr (1993) A reagent for the single-step simultaneous isolation of RNA, DNA and proteins from cell and tissue samples. Biotechniques 15(3):532-537.
Clough, Steven J. and Bent, Andrew F. (1998) Floral dip: a simplified method for Agrobacterium-mediated transformation of Arabidopsis thaliana. Plant J 16(6):735-743.
Deikman, J. et al., (1992) Organization of Ripening and Ethylene Regulatory Regions in a Fruit-Specific Promoter from Tomato (*Lycopersicon esculentum*). Plant Physiol 100(4):2013-2017.
Fillati, JoAnne J. et al., (1987) Efficient transfer of glyphosate tolerance gene into tomato using a binary *Agrobacterium tumefaciens* vector. Nature BioTechnology 5:726-730.
Fraser, Paul D. et al., (2000) Technical advance: application of high-performance liquid chromatography with photodiode array detection to the metabolic profiling of plant isoprenoids. Plant J 24(4):551-558.

(Continued)

*Primary Examiner* — Lee A Visone
*Assistant Examiner* — Weihua Fan

(57) ABSTRACT

The present invention provides transgenic plants comprising 3-Deoxy-D-Arabino-Heptulosonate 7-Phosphate (DAHP) Synthase that is insensitive to feedback inhibition, particularly to feedback inhibition by phenylalanine, producing increased amounts of the Shikimate pathway primary and secondary metabolites, including aromatic amino acids compared to corresponding non-transgenic plants.

13 Claims, 19 Drawing Sheets

(56) References Cited

OTHER PUBLICATIONS

Ger, Ya-Ming et al., (1994) A single Ser-180 mutation desensitizes feedback inhibition of the phenylalanine-sensitive 3-deoxy-D-arabino-heptulosonate 7-phosphate (DAHP) synthetase in *Escherichia coli*. J Biochem 116(5):986-990.

Gilchrist, David and Kosuge, T. Aromatic Amino Acid Biosynthesis and its Regulation. In: the Biochemistry of Plants, B.J. Miflin, ed. Academic Press, New York, 1980 vol. 5 pp. 507-531.

Gleave, Andrew P. (1992) A versatile binary vector system with a T-DNA organisational structure conducive to efficient integration of cloned DNA into the plant genome. Plant Mol Biol 20(6):1203-1207.

Gorlach, Jorn et al., (1993) Differential expression of tomato (*Lycopersicon esculentum* L.) genes encoding shikimate pathway isoenzymes. II. Chorismate synthase. Plant Mol Biol 23(4):707-716.

Harmer, Stacy L. et al., (2000) Orchestrated transcription of key pathways in Arabidopsis by the circadian clock. Science 290(5499):2110-2113.

Herrmann, Klaus M. and Weaver, Lisa M. (1999) The shikimate pathway. Annu Rev Plant Physiol Plant Mol Biol 50:473-503.

Hochberg, Yosef and Benjamini, Yoav (1990) More powerful procedures for multiple significance testing. Stat Med 9(7):811-818.

Hu, Changyun et al., (2003) Mutation analysis of the feedback inhibition site of phenylalanine-sensitive 3-deoxy-D-arabino-heptulosonate 7-phosphate synthase of *Escherichia coli*. J Basic Microbiol 43(5):399-406.

Irizarry, Rafael A. et al., (2003) Exploration, normalization, and summaries of high density oligonucleotide array probe level data. Biostatistics 4(2):249-264.

Jones, J. D. et al., (1995) Impaired Wound Induction of 3-Deoxy-D-arabino-heptulosonate-7-phosphate (DAHP) Synthase and Altered Stem Development in Transgenic Potato Plants Expressing a DAHP Synthase Antisense Construct. Plant Physiol 108(4):1413-1421.

Keith, Brian et al., (1991) Differential induction of 3-deoxy-D-arabino-heptulosonate 7-phosphate synthase genes in Arabidopsis thaliana by wounding and pathogenic attack. Proc Natl Acad Sci USA 88(19):8821-8825.

Kisaka, Hiroaki et al., (1996) Characterization of interfamilial somatic hybrids between 5-methyltryptophan-resistant (5MT-resistant) rice (*Oryza sativa* L.) and 5MT-sensitive carrot (*Daucus carota* L.); Expression of resistance to 5MT by somatic hybrids. Breed Sci 46:221-226.

Li, J. J and Last, R.L. (1996) The Arabidopsis thaliana trp5 mutant has a feedback-resistant anthranilate synthase and elevated soluble tryptophan. Plant Physiol 110(1):51-59.

Malitsky, Sergey et al., (2008) The transcript and metabolite networks affected by the two clades of Arabidopsis glucosinolate biosynthesis regulators. Plant Physiol 148(4):2021-2049.

McCormic, Sheila (1991) Transformation of tomato with *Agrobacterium tumefaciens*. Plant Tissue Culture Manual B6:1-9.

Mintz-Oron, Shira et al., (2008) Gene expression and metabolism in tomato fruit surface tissues. Plant Physiol 147 (2):823-851.

Muday, Gloria K. and Herrmann, Klaus M. (1992) Wounding Induces One of Two Isoenzymes of 3-Deoxy-d-arabino-Heptulosonate 7-Phosphate Synthase in *Solanum tuberosum* L. Plant Physiology 98(2):496-500.

Pribat, Anne et al., (2010) Nonflowering plants possess a unique folate-dependent phenylalanine hydroxylase that is localized in chloroplasts. Plant cell 22(10):3410-3422.

Rippert, Pascal and Matringe, Michel (2002) Purification and kinetic analysis of the two recombinant arogenate dehydrogenase isoforms of Arabidopsis thaliana. Eur J Biochem 269(19):4753-4761.

Saeed, A. I. et al., (2003) TM4: a free, open-source system for microarray data management and analysis. Biotechniques 34(2):374-378.

Scholz, M. et al., (2004) Metabolite fingerprinting: detecting biological features by independent component analysis. Bioinformatics 20(15):2447-2454.

Shaul, Orit and Galili, Gad (1993) Concerted regulation of lysine and threonine synthesis in tobacco plants expressing bacterial feedback-insensitive aspartate kinase and dihydrodipicolinate synthase. Plant Mol Biol 23 (4):759-768.

Shevtsova, Z. et al., (2006) Evaluation of epitope tags for protein detection after in vivo CNS gene transfer. Eur J Neurosci 23(8):1961-1969.

Smith, Colin A. et al., (2006) XCMS: processing mass spectrometry data for metabolite profiling using nonlinear peak alignment, matching, and identification. Anal Chem 78(3):779-787.

Tzin, Vered et al., (2009) Expression of a bacterial bi-functional chorismate mutase/prephenate dehydratase modulates primary and secondary metabolism associated with aromatic amino acids in Arabidopsis. Plant J 60 (1):156-167.

Tzin, Vered and Galili, Gad (2010) The biosynthetic pathways for shikimate and aromatic amino acids in Arabidopsis thaliana. Arabidopsis Book. 8:e0132 (18 pages).

Usadel, Bjorn et al., (2005) Extension of the visualization tool MapMan to allow statistical analysis of arrays, display of corresponding genes, and comparison with known responses. Plant Physiol 138(3):1195-1204.

Usadel, Bjorn et al., (2006) PageMan: an interactive ontology tool to generate, display, and annotate overview graphs for profiling experiments. BMC Bioinformatics 7:535 (8pages).

Wallace, B. J. and Pittard, James (1967) Genetic and biochemical analysis of the isoenzymes concerned in the first reaction of aromatic biosynthesis in *Escherichia coli*. J Bacteriol 93(1):237-244.

Widholm, J. M. (1972) Anthranilate synthetase from 5-methyltryptophan-susceptible and -resistant cultured Daucus carota cells. Biochim Biophys Acta 279(1):48-57.

Xu, Jiangfeng et al., (2004) Requirement of the N-terminus for dimer formation of phenylalanine-sensitive 3-deoxy-D-arabino-heptulosonate synthase AroG of *Escherichia coli*. J Basic Microbiol 44(5):400-406.

Zhao, Lingxia et al., (2009) Molecular evolution of the E8 promoter in tomato and some of its relative wild species. J Biosci 34(1):71-83.

ISR of PCT/IL2011/000535 dated Oct. 17, 2011.

Office Action dated Aug. 4, 2015 From the Israel Patent Office Re. Application No. 223852.

Translation dated Aug. 25, 2015 of Office Action dated Aug. 4, 2015 From the Israel Patent Office Re. Application No. 223852.

Communication Pursuant to Article 94(3) EPC dated Feb. 29, 2016 From the European Patent Office Re. Application No. 11741693.3.

Communication Pursuant to Article 94(3) EPC dated Dec. 5, 2016 From the European Patent Office Re. Application No. 11741693.3. (4 Pages).

\* cited by examiner

Figure 2A Original sequence: 35S-PRO | TP | AroG<sub>WT</sub> | HA | OCS-TER

Point mutation in the allosteric site

Figure 2B: 35S/E8-PRO | TP | AroG<sub>Leu175Gln</sub> | HA | OCS-TER

Figure 2C: 35S/E8-PRO | TP | AroG<sub>Phe209Ala</sub> | HA | OCS-TER

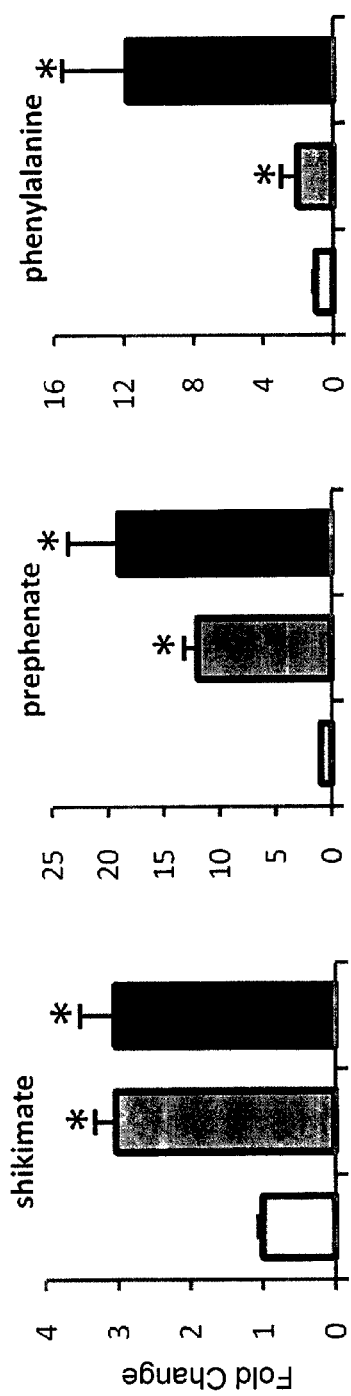
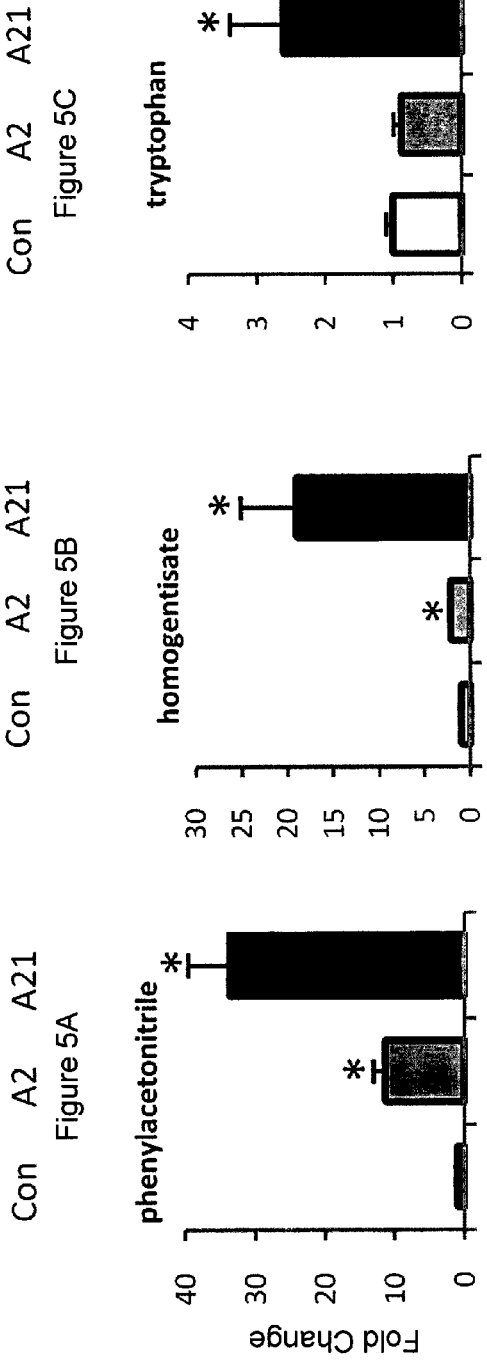

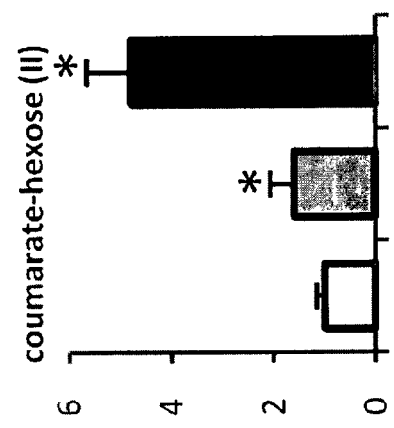
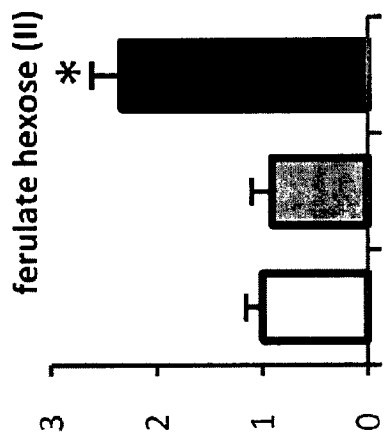
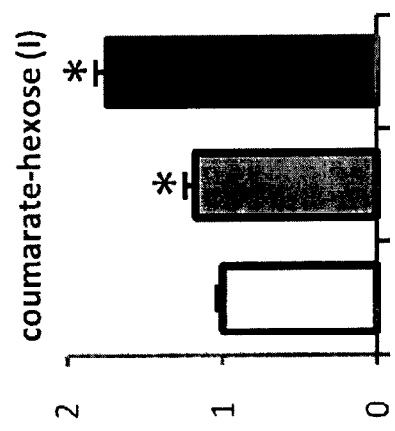
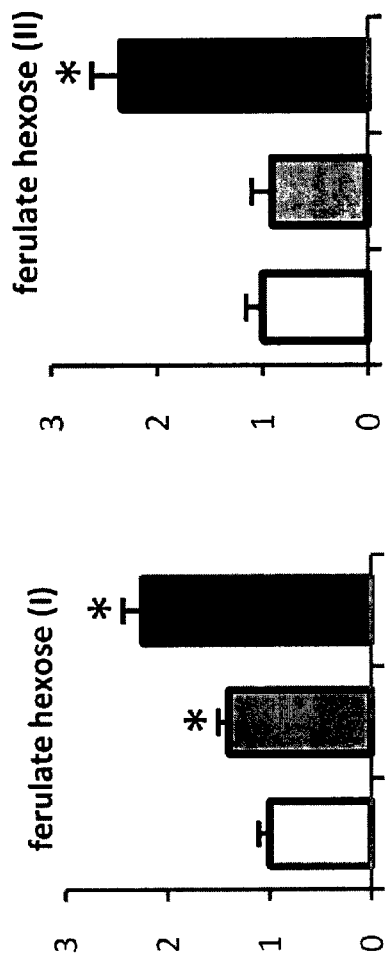
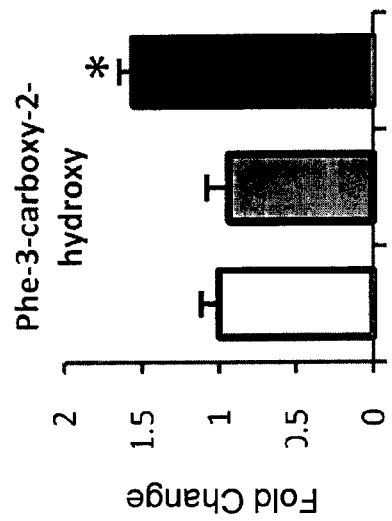
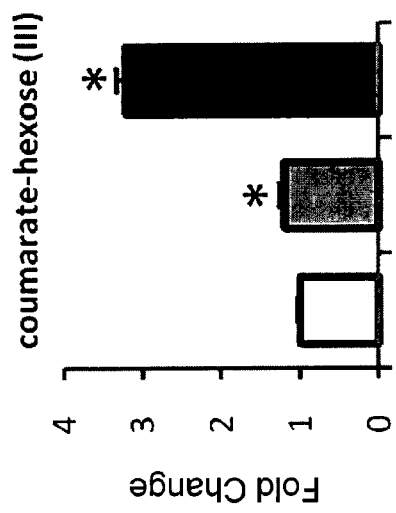

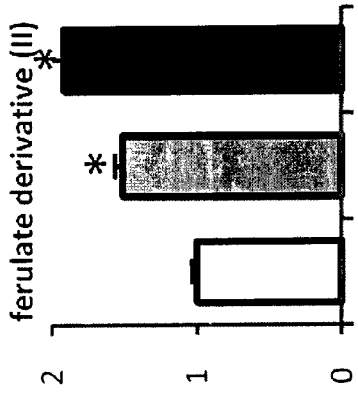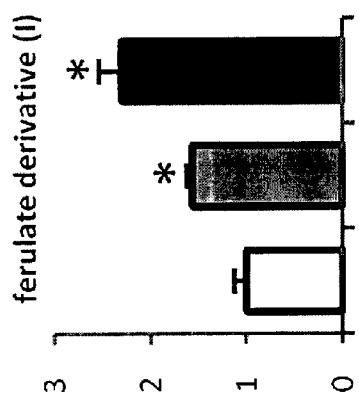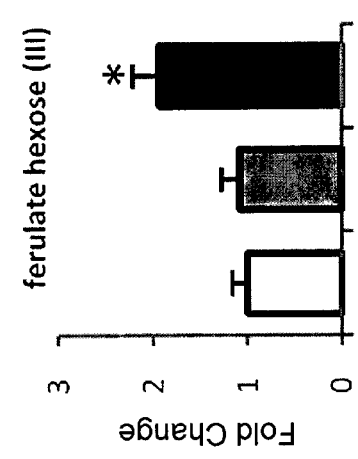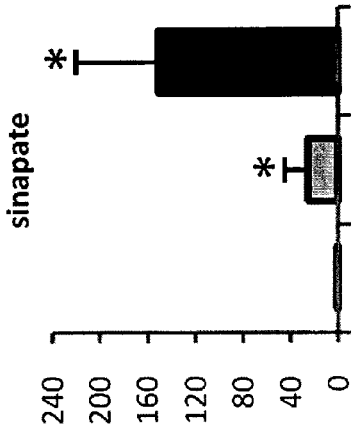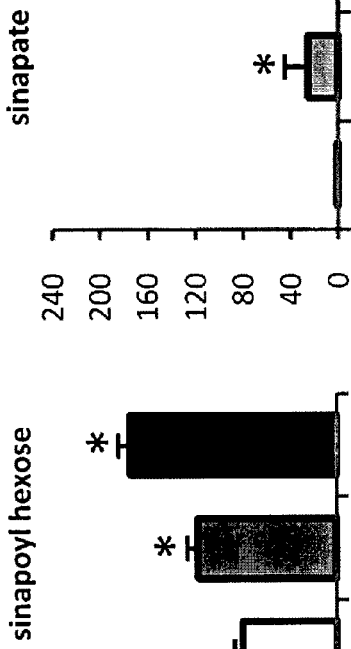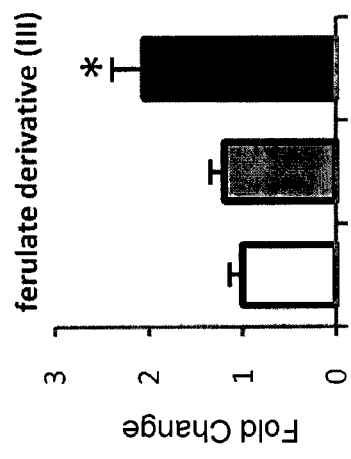

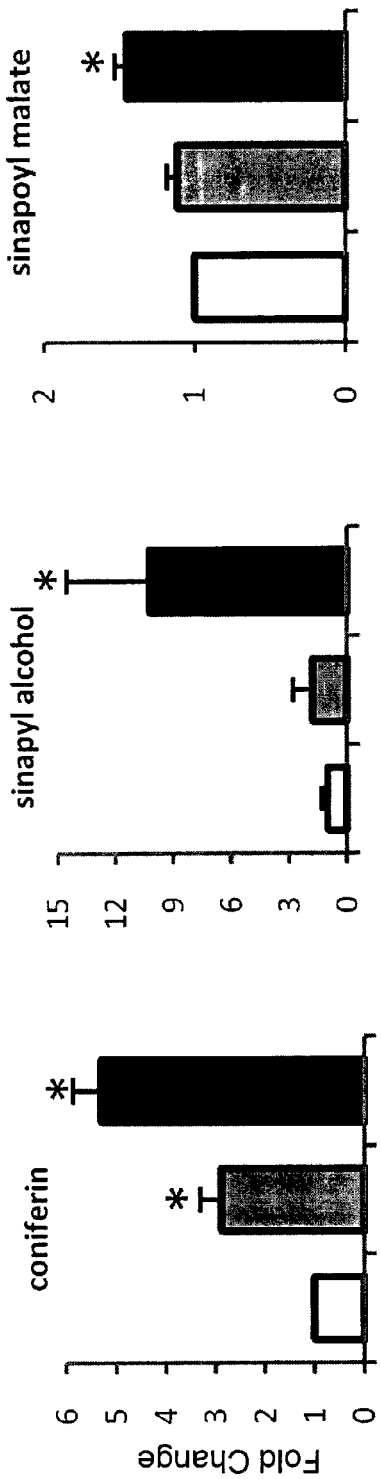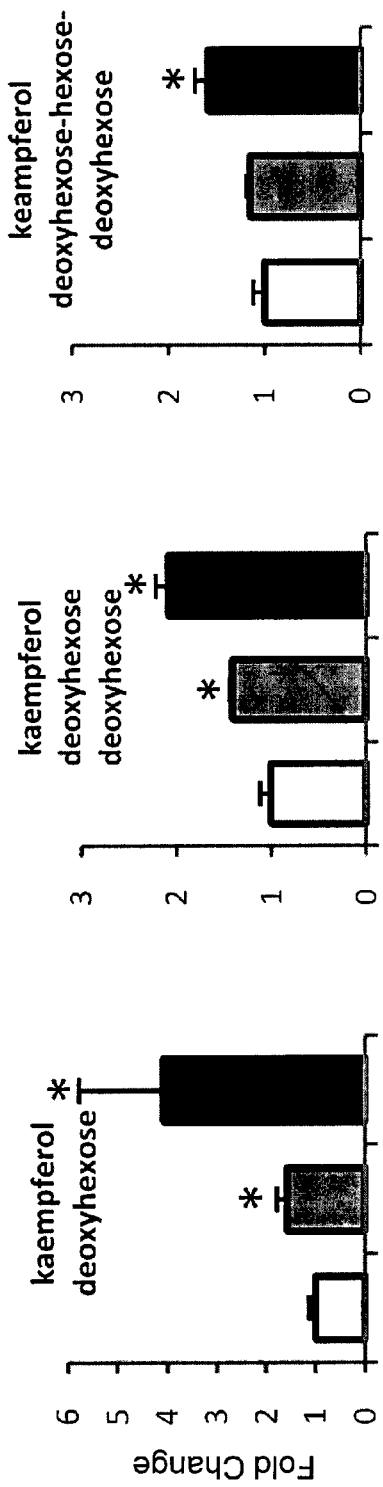

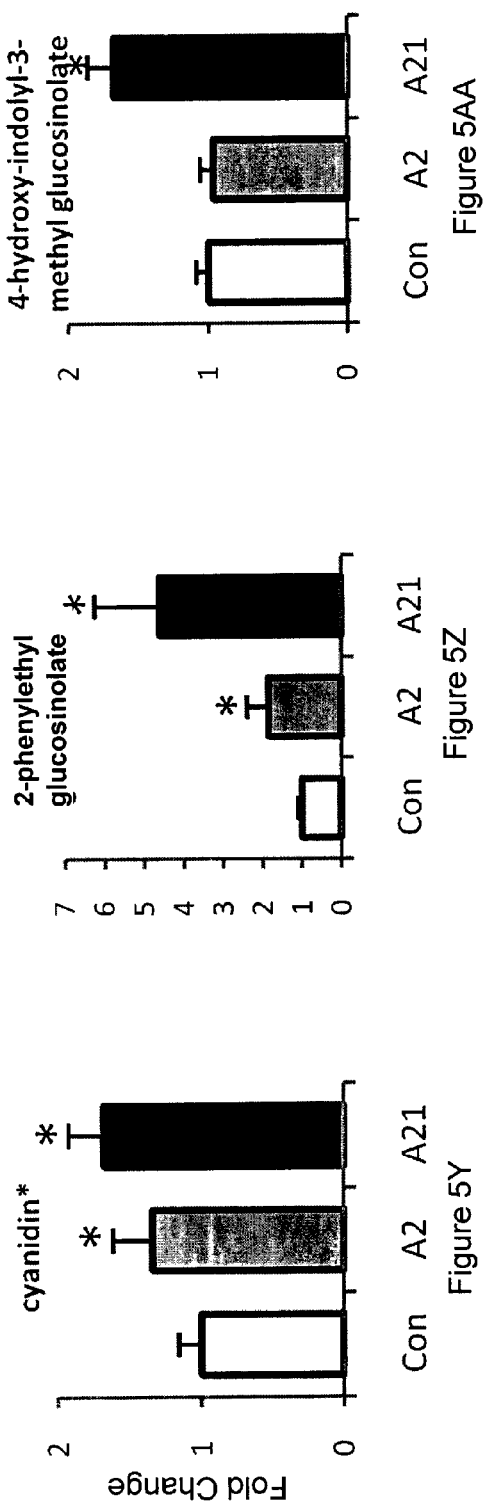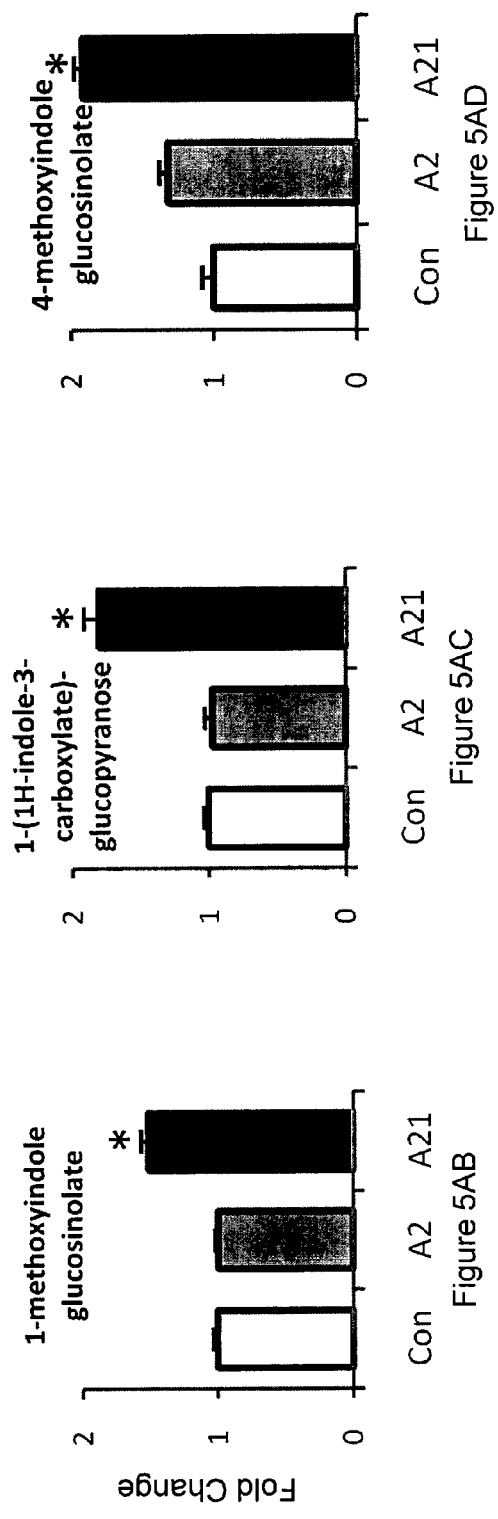

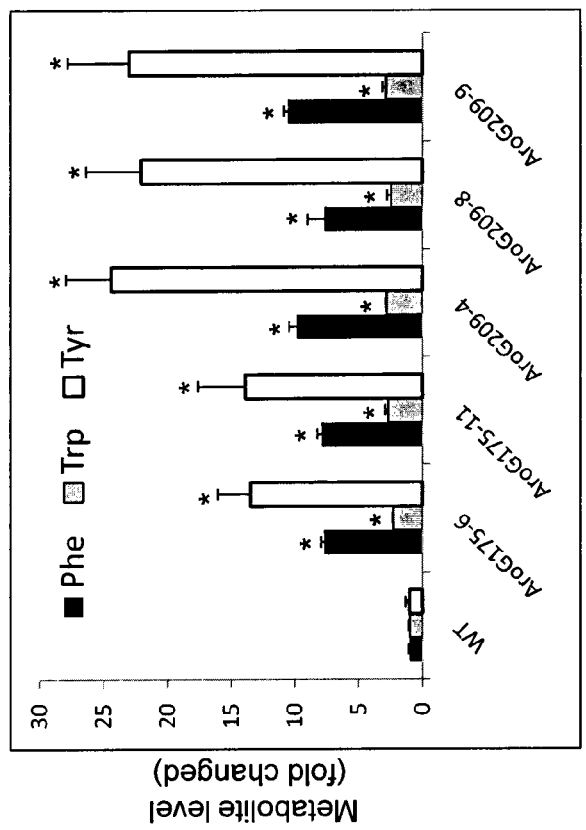
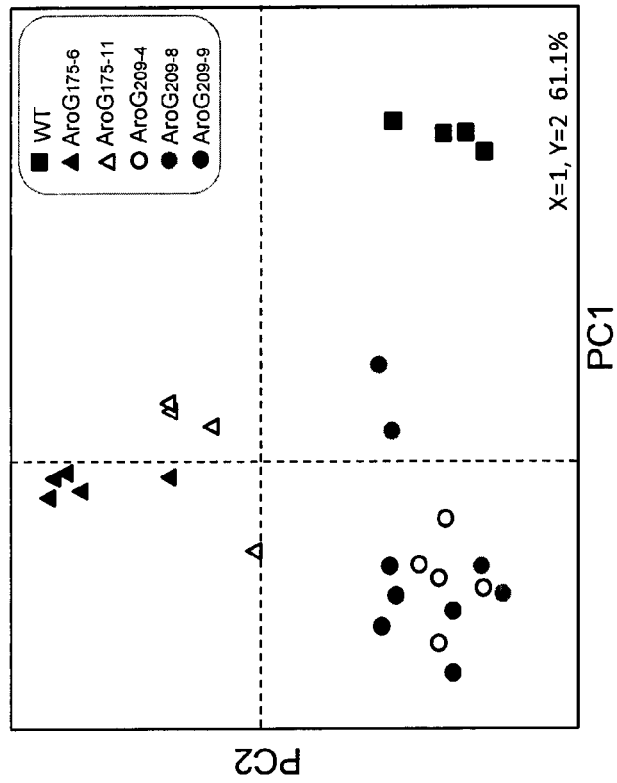
Figure 8B
Figure 8A

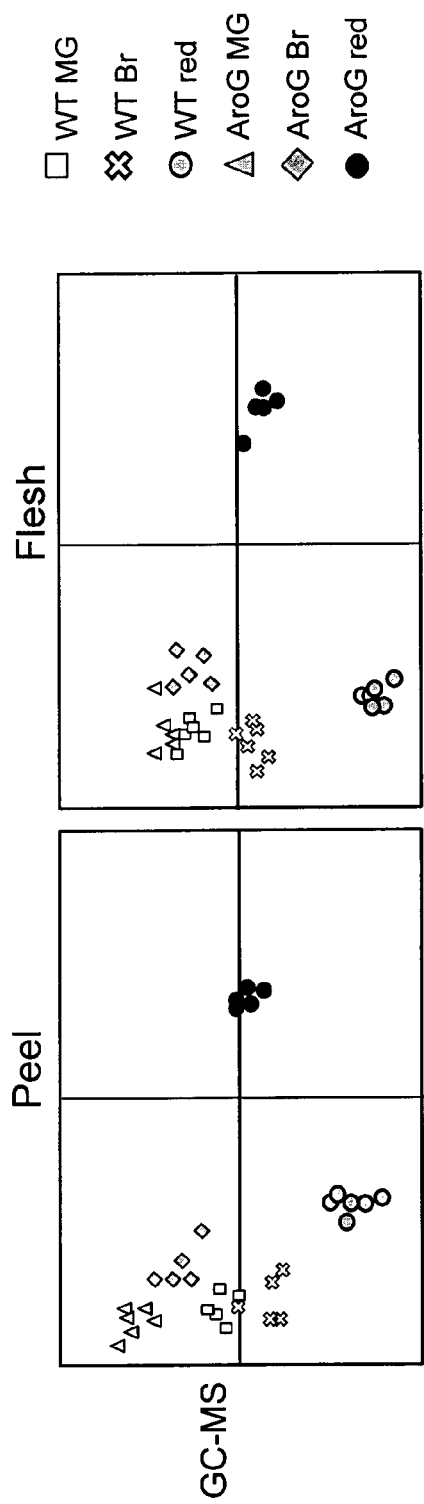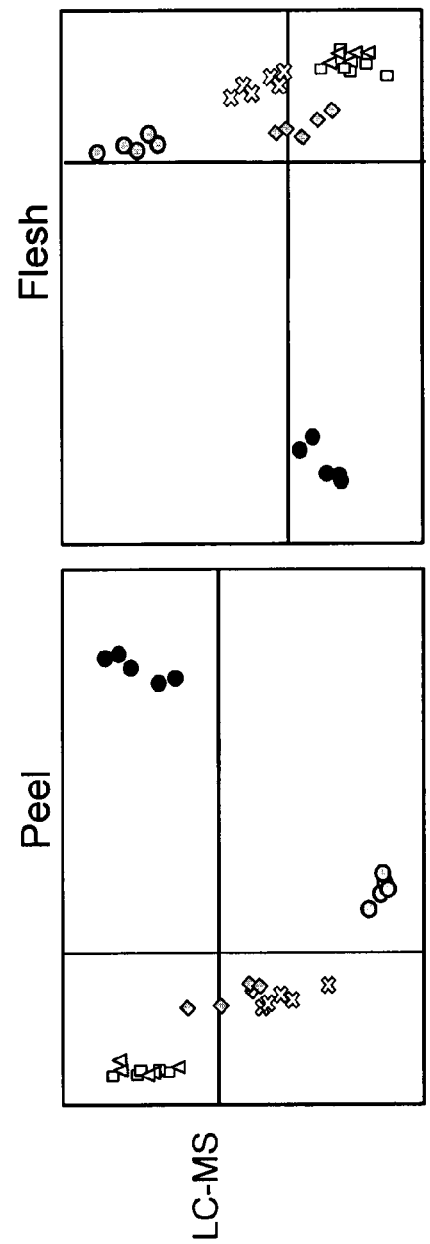
Figure 9A
Figure 9B

SEQUENCE LISTING

<160> NUMBER OF SEQ ID NOS: 16

<210> SEQ ID NO 1
<211> LENGTH: 350
<212> TYPE: PRT
<213> ORGANISM: Escherichia coli

<400> SEQUENCE: 1

Met Asn Tyr Gln Asn Asp Asp Leu Arg Ile Lys Glu Ile Lys Glu Leu

-continued

```
1               5                   10                  15
Leu Pro Pro Val Ala Leu Leu Glu Lys Phe Pro Ala Thr Glu Asn Ala
                20                  25                  30
Ala Asn Thr Val Ala His Ala Arg Lys Ala Ile His Lys Ile Leu Lys
                35                  40                  45
Gly Asn Asp Asp Arg Leu Leu Val Val Ile Gly Pro Cys Ser Ile His
 50                  55                  60
Asp Pro Val Ala Ala Lys Glu Tyr Ala Thr Arg Leu Leu Ala Leu Arg
 65                  70                  75                  80
Glu Glu Leu Lys Asp Glu Leu Glu Ile Val Met Arg Val Tyr Phe Glu
                85                  90                  95
Lys Pro Arg Thr Thr Val Gly Trp Lys Gly Leu Ile Asn Asp Pro His
                100                 105                 110
Met Asp Asn Ser Phe Gln Ile Asn Asp Gly Leu Arg Ile Ala Arg Lys
                115                 120                 125
Leu Leu Leu Asp Ile Asn Asp Ser Gly Leu Pro Ala Ala Gly Glu Phe
                130                 135                 140
Leu Asp Met Ile Thr Pro Gln Tyr Leu Ala Asp Leu Met Ser Trp Gly
145                 150                 155                 160
Ala Ile Gly Ala Arg Thr Thr Glu Ser Gln Val His Arg Glu Leu Ala
                165                 170                 175
Ser Gly Leu Ser Cys Pro Val Gly Phe Lys Asn Gly Thr Asp Gly Thr
                180                 185                 190
Ile Lys Val Ala Ile Asp Ala Ile Asn Ala Ala Gly Ala Pro His Cys
                195                 200                 205
Phe Leu Ser Val Thr Lys Trp Gly His Ser Ala Ile Val Asn Thr Ser
210                 215                 220
Gly Asn Gly Asp Cys His Ile Ile Leu Arg Gly Gly Lys Glu Pro Asn
225                 230                 235                 240
Tyr Ser Ala Lys His Val Ala Glu Val Lys Glu Gly Leu Asn Lys Ala
                245                 250                 255
Gly Leu Pro Ala Gln Val Met Ile Asp Phe Ser His Ala Asn Ser Ser
                260                 265                 270
Lys Gln Phe Lys Lys Gln Met Asp Val Cys Ala Asp Val Cys Gln Gln
                275                 280                 285
Ile Ala Gly Gly Glu Lys Ala Ile Ile Gly Val Met Val Glu Ser His
                290                 295                 300
Leu Val Glu Gly Asn Gln Ser Leu Glu Ser Gly Glu Pro Leu Ala Tyr
305                 310                 315                 320
Gly Lys Ser Ile Thr Asp Ala Cys Ile Gly Trp Glu Asp Thr Asp Ala
                325                 330                 335
Leu Leu Arg Gln Leu Ala Asn Ala Val Lys Ala Arg Arg Gly
                340                 345                 350

<210> SEQ ID NO 2
<211> LENGTH: 350
<212> TYPE: PRT
<213> ORGANISM: Artificial Sequence
<220> FEATURE:
<223> OTHER INFORMATION: E.coli AroG175 mutant

<400> SEQUENCE: 2

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
```

```
                20                  25                  30
Ala Asn Thr Val Ala His Ala Arg Lys Ala Ile His Lys Ile Leu Lys
             35                  40                  45

Gly Asn Asp Asp Arg Leu Leu Val Val Ile Gly Pro Cys Ser Ile His
 50                  55                  60

Asp Pro Val Ala Ala Lys Glu Tyr Ala Thr Arg Leu Leu Ala Leu Arg
 65                  70                  75                  80

Glu Glu Leu Lys Asp Glu Leu Glu Ile Val Met Arg Val Tyr Phe Glu
                 85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
            115                 120                 125

Leu Leu Leu Asp Ile Asn Asp Ser Gly Leu Pro Ala Ala Gly Glu Phe
            130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Gln Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
            195                 200                 205

Phe Leu Ser Val Thr Lys Trp Gly His Ser Ala Ile Val Asn Thr Ser
210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
            275                 280                 285

Ile Ala Gly Gly Glu Lys Ala Ile Ile Gly Val Met Val Glu Ser His
290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350
```

<210> SEQ ID NO 3
<211> LENGTH: 1050
<212> TYPE: DNA
<213> ORGANISM: Artificial Sequence
<220> FEATURE:
<223> OTHER INFORMATION: Polynucleotide encoding E. coli AroG175 mutant

<400> SEQUENCE: 3

```
atgaattatc agaacgacga tttacgcatc aaagaaatca agagttact  tcctcctgtc    60 gcattgctgg aaaaattccc cgctactgaa aatgccgcga atacggttgc ccatgcccga   120
aaagcgatcc ataagatcct gaaaggtaat gatgatcgcc tgttggttgt gattggccca   180
tgctcaattc atgatcctgt cgcggcaaaa gagtatgcca ctcgcttgct ggcgctgcgt   240
```

```
gaagagctga aagatgagct ggaaatcgta atgcgcgtct attttgaaaa gccgcgtacc    300
acggtgggct ggaaagggct gattaacgat ccgcatatgg ataatagctt ccagatcaac    360
gacggtctgc gtatagcccg taaattgctg cttgatatta cgacagcgg tctgccagcg     420
gcaggtgagt ttctcgatat gatcacccca caatatctcg ctgacctgat gagctggggc    480
gcaattggcg cacgtaccac cgaatcgcag gtgcaccgcg aacaggcatc agggctttct    540
tgtccggtcg gcttcaaaaa tggcaccgac ggtacgatta agtggctat cgatgccatt     600
aatgccgccg gtgcgccgca ctgcttcctg tccgtaacga atgggggca ttcggcgatt     660
gtgaatacca gcgtaacgg cgattgccat atcattctgc gcggcggtaa agagcctaac     720
tacagcgcga agcacgttgc tgaagtgaaa gaagggctga caaagcagg cctgccagca     780
caggtgatga tcgatttcag ccatgctaac tcgtccaaac aattcaaaaa gcagatggat    840
gtttgtgctg acgtttgcca gcagattgcc ggtggcgaaa aggccattat tggcgtgatg    900
gtggaaagcc atctggtgga aggcaatcag agcctcgaga gcggggagcc gctggcctac    960
ggtaagagca tcaccgatgc ctgcatcggc tgggaagata ccgatgctct gttacgtcaa    1020
ctggcgaatg cagtaaaagc gcgtcgcggg                                    1050

<210> SEQ ID NO 4
<211> LENGTH: 350
<212> TYPE: PRT
<213> ORGANISM: Artificial Sequence
<220> FEATURE:
<223> OTHER INFORMATION: E. coli AroG209 mutant

<400> SEQUENCE: 4

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
                20                  25                  30

Ala Asn Thr Val Ala His Ala Arg Lys Ala Ile His Lys Ile Leu Lys
            35                  40                  45

Gly Asn Asp Asp Arg Leu Leu Val Val Ile Gly Pro Cys Ser Ile His
        50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
    130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Ala Leu Ser Val Thr Lys Trp Gly His Ser Ala Ile Val Asn Thr Ser
```

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
            245                 250                 255

Gly Leu Pro Ala Gln Val Met Ile Asp Phe Ser His Ala Asn Ser Ser
        260                 265                 270

Lys Gln Phe Lys Lys Gln Met Asp Val Cys Ala Asp Val Cys Gln Gln
    275                 280                 285

Ile Ala Gly Gly Glu Lys Ala Ile Ile Gly Val Met Val Glu Ser His
290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
            325                 330                 335

Leu Leu Arg Gln Leu Ala Asn Ala Val Lys Ala Arg Arg Gly
        340                 345                 350

<210> SEQ ID NO 5
<211> LENGTH: 1052
<212> TYPE: DNA
<213> ORGANISM: Artificial Sequence
<220> FEATURE:
<223> OTHER INFORMATION: Polynucleotide encoding E. coli Arog209 mutant

<400> SEQUENCE: 5
tgatgaatta tcagaacgac gatttacgca tcaaagaaat caaagagtta cttcctcctg        60
tcgcattgct ggaaaaattc cccgctactg aaaatgccgc gaatacggtt gcccatgccc       120
gaaaagcgat cctaagatc ctgaaaggta atgatgatcg cctgttggtt gtgattggcc        180
catgctcaat tcatgatcct gtcgcggcaa aagagtatgc cactcgcttg ctggcgctgc       240
gtgaagagct gaaagatgag ctggaaatcg taatgcgcgt ctattttgaa agccgcgta       300 ccacggtggg ctggaaaggg ctgattaacg atccgcatat ggataatagc ttccagatca       360
acgacggtct gcgtatagcc cgtaaattgc tgcttgatat taacgacagc ggtctgccag       420
cggcaggtga gtttctcgat atgatcaccc cacaatatct cgctgacctg atgagctggg       480
gcgcaattgg cgcacgtacc accgaatcgc aggtgcaccg cgaactggca tcagggcttt       540
cttgtccggt cggcttcaaa atggcaccg acggtacgat taaagtggct atcgatgcca       600
ttaatgccgc cggtgcgccg cactcgcgccc tgtccgtaac gaaatggggg cattcggcga       660
ttgtgaatac cagcggtaac ggcgattgcc atatcattct gcgcggcggt aaagagccta       720
actacagcgc gaagcacgtt gctgaagtga agaagggct aacaaagca ggcctgccag        780 cacaggtgat gatcgatttc agccatgcta actcgtccaa acaattcaaa aagcagatgg       840
atgtttgtgc tgacgtttgc cagcagattg ccggtggcga aaaggccatt attggcgtga       900
tggtggaaag ccatctggtg gaaggcaatc agagcctcga gagcggggag ccgctggcct       960
acggtaagag catcaccgat gcctgcatcg gctgggaaga taccgatgct ctgttacgtc      1020
aactggcgaa tgcagtaaaa gcgcgtcgcg gg                                    1052

<210> SEQ ID NO 6
<211> LENGTH: 187
<212> TYPE: DNA
<213> ORGANISM: Artificial Sequence
<220> FEATURE:
<223> OTHER INFORMATION: Polynucleotide encoding pea rbcS3 plastid transit peptide

<400> SEQUENCE: 6

```
gtcgactaga aaatggcttc tatgatatcc tcttcagctg tgactacagt cagccgtgct    60
tctacggtgc aatcggccgc ggtggctcca ttcggcggcc tcaaatccat gactggattc   120
ccagttaaga aggtcaacac tgacattact tccattacaa gcaatggtgg aagagtaaag   180
tgcatgc                                                             187
```

<210> SEQ ID NO 7
<211> LENGTH: 105
<212> TYPE: DNA
<213> ORGANISM: Artificial Sequence
<220> FEATURE:
<223> OTHER INFORMATION: Polynucleotide sequence encoding three repeats of HA epitope tag

<400> SEQUENCE: 7

```
atcttttacc catacgatgt tcctgactat gcgggctatc cctatgacgt cccggactat    60
gcaggatcct atccatatga cgttccagat tacgctgctc agtag                   105
```

<210> SEQ ID NO 8
<211> LENGTH: 445
<212> TYPE: PRT
<213> ORGANISM: Artificial Sequence
<220> FEATURE:
<223> OTHER INFORMATION: TP-AroG175-3HA polypeptide

<400> SEQUENCE: 8

```
Met Ala Ser Met Ile Ser Ser Ala Val Thr Thr Val Ser Arg Ala
1               5                   10                  15

Ser Thr Val Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Leu Met Asn Tyr Gln Asn
    50                  55                  60

Asp Asp Leu Arg Ile Lys Glu Ile Lys Glu Leu Leu Pro Pro Val Ala
65                  70                  75                  80

Leu Leu Glu Lys Phe Pro Ala Thr Glu Asn Ala Ala Asn Thr Val Ala
                85                  90                  95

His Ala Arg Lys Ala Ile His Lys Ile Leu Lys Gly Asn Asp Asp Arg
            100                 105                 110

Leu Leu Val Val Ile Gly Pro Cys Ser Ile His Asp Pro Val Ala Ala
        115                 120                 125

Lys Glu Tyr Ala Thr Arg Leu Leu Ala Leu Arg Glu Glu Leu Lys Asp
    130                 135                 140

Glu Leu Glu Ile Val Met Arg Val Tyr Phe Glu Lys Pro Arg Thr Thr
145                 150                 155                 160

Val Gly Trp Lys Gly Leu Ile Asn Asp Pro His Met Asp Asn Ser Phe
                165                 170                 175

Gln Ile Asn Asp Gly Leu Arg Ile Ala Arg Lys Leu Leu Leu Asp Ile
            180                 185                 190

Asn Asp Ser Gly Leu Pro Ala Ala Gly Glu Phe Leu Asp Met Ile Thr
        195                 200                 205

Pro Gln Tyr Leu Ala Asp Leu Met Ser Trp Gly Ala Ile Gly Ala Arg
    210                 215                 220
```

```
Thr Thr Glu Ser Gln Val His Arg Glu Gln Ala Ser Gly Leu Ser Cys
225                 230                 235                 240

Pro Val Gly Phe Lys Asn Gly Thr Asp Gly Thr Ile Lys Val Ala Ile
            245                 250                 255

Asp Ala Ile Asn Ala Ala Gly Ala Pro His Cys Phe Leu Ser Val Thr
        260                 265                 270

Lys Trp Gly His Ser Ala Ile Val Asn Thr Ser Gly Asn Gly Asp Cys
    275                 280                 285

His Ile Ile Leu Arg Gly Gly Lys Glu Pro Asn Tyr Ser Ala Lys His
290                 295                 300

Val Ala Glu Val Lys Glu Gly Leu Asn Lys Ala Gly Leu Pro Ala Gln
305                 310                 315                 320

Val Met Ile Asp Phe Ser His Ala Asn Ser Ser Lys Gln Phe Lys Lys
            325                 330                 335

Gln Met Asp Val Cys Ala Asp Val Cys Gln Gln Ile Ala Gly Gly Glu
        340                 345                 350

Lys Ala Ile Ile Gly Val Met Val Glu Ser His Leu Val Glu Gly Asn
    355                 360                 365

Gln Ser Leu Glu Ser Gly Glu Pro Leu Ala Tyr Gly Lys Ser Ile Thr
370                 375                 380

Asp Ala Cys Ile Gly Trp Glu Asp Thr Asp Ala Leu Leu Arg Gln Leu
385                 390                 395                 400

Ala Asn Ala Val Lys Ala Arg Arg Gly Glu Phe Ile Phe Tyr Pro Tyr
            405                 410                 415

Asp Val Pro Asp Tyr Ala Gly Tyr Pro Tyr Asp Val Pro Asp Tyr Ala
        420                 425                 430

Gly Ser Tyr Pro Tyr Asp Val Pro Asp Tyr Ala Ala Gln
    435                 440                 445

<210> SEQ ID NO 9
<211> LENGTH: 445
<212> TYPE: PRT
<213> ORGANISM: Artificial Sequence
<220> FEATURE:
<223> OTHER INFORMATION: TP-AroG209-3HA polypeptide

<400> SEQUENCE: 9

Met Ala Ser Met Ile Ser Ser Ser Ala Val Thr Thr Val Ser Arg Ala
1               5                   10                  15

Ser Thr Val Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Leu Met Asn Tyr Gln Asn
    50                  55                  60

Asp Asp Leu Arg Ile Lys Glu Ile Lys Glu Leu Leu Pro Pro Val Ala
65                  70                  75                  80

Leu Leu Glu Lys Phe Pro Ala Thr Glu Asn Ala Ala Asn Thr Val Ala
            85                  90                  95

His Ala Arg Lys Ala Ile His Lys Ile Leu Lys Gly Asn Asp Asp Arg
        100                 105                 110

Leu Leu Val Val Ile Gly Pro Cys Ser Ile His Asp Pro Val Ala Ala
    115                 120                 125

Lys Glu Tyr Ala Thr Arg Leu Leu Ala Leu Arg Glu Glu Leu Lys Asp
130                 135                 140
```

```
Glu Leu Glu Ile Val Met Arg Val Tyr Phe Glu Lys Pro Arg Thr Thr
145                 150                 155                 160

Val Gly Trp Lys Gly Leu Ile Asn Asp Pro His Met Asp Asn Ser Phe
            165                 170                 175

Gln Ile Asn Asp Gly Leu Arg Ile Ala Arg Lys Leu Leu Leu Asp Ile
            180                 185                 190

Asn Asp Ser Gly Leu Pro Ala Ala Gly Glu Phe Leu Asp Met Ile Thr
            195                 200                 205

Pro Gln Tyr Leu Ala Asp Leu Met Ser Trp Gly Ala Ile Gly Ala Arg
            210                 215                 220

Thr Thr Glu Ser Gln Val His Arg Glu Leu Ala Ser Gly Leu Ser Cys
225                 230                 235                 240

Pro Val Gly Phe Lys Asn Gly Thr Asp Gly Thr Ile Lys Val Ala Ile
            245                 250                 255

Asp Ala Ile Asn Ala Ala Gly Ala Pro His Cys Ala Leu Ser Val Thr
            260                 265                 270

Lys Trp Gly His Ser Ala Ile Val Asn Thr Ser Gly Asn Gly Asp Cys
            275                 280                 285

His Ile Ile Leu Arg Gly Gly Lys Glu Pro Asn Tyr Ser Ala Lys His
            290                 295                 300

Val Ala Glu Val Lys Glu Gly Leu Asn Lys Ala Gly Leu Pro Ala Gln
305                 310                 315                 320

Val Met Ile Asp Phe Ser His Ala Asn Ser Ser Lys Gln Phe Lys Lys
                325                 330                 335

Gln Met Asp Val Cys Ala Asp Val Cys Gln Gln Ile Ala Gly Gly Glu
            340                 345                 350

Lys Ala Ile Ile Gly Val Met Val Glu Ser His Leu Val Glu Gly Asn
355                 360                 365

Gln Ser Leu Glu Ser Gly Glu Pro Leu Ala Tyr Gly Lys Ser Ile Thr
            370                 375                 380

Asp Ala Cys Ile Gly Trp Glu Asp Thr Asp Ala Leu Leu Arg Gln Leu
385                 390                 395                 400

Ala Asn Ala Val Lys Ala Arg Arg Gly Glu Phe Ile Phe Tyr Pro Tyr
                405                 410                 415

Asp Val Pro Asp Tyr Ala Gly Tyr Pro Tyr Asp Val Pro Asp Tyr Ala
            420                 425                 430

Gly Ser Tyr Pro Tyr Asp Val Pro Asp Tyr Ala Ala Gln
            435                 440                 445

<210> SEQ ID NO 10
<211> LENGTH: 31
<212> TYPE: DNA
<213> ORGANISM: Artificial Sequence
<220> FEATURE:
<223> OTHER INFORMATION: Synthetic primer

<400> SEQUENCE: 10
catgcatgct gatgaattat cagaacgacg a                              31

<210> SEQ ID NO 11
<211> LENGTH: 27
<212> TYPE: DNA
<213> ORGANISM: Artificial Sequence
<220> FEATURE:
<223> OTHER INFORMATION: Synthetic primer

<400> SEQUENCE: 11
```

```
ggaattcccc gcgacgcgct tttactg                                          27
```

<210> SEQ ID NO 12
<211> LENGTH: 27
<212> TYPE: DNA
<213> ORGANISM: Artificial Sequence
<220> FEATURE:
<223> OTHER INFORMATION: Synthetic primer

<400> SEQUENCE: 12

```
gtgcaccgcg aacaggcatc agggctt                                          27
```

<210> SEQ ID NO 13
<211> LENGTH: 27
<212> TYPE: DNA
<213> ORGANISM: Artificial Sequence
<220> FEATURE:
<223> OTHER INFORMATION: Synthetic primer

<400> SEQUENCE: 13

```
aagccctgat gcctgttcgc ggtgcac                                          27
```

<210> SEQ ID NO 14
<211> LENGTH: 27
<212> TYPE: DNA
<213> ORGANISM: Artificial Sequence
<220> FEATURE:
<223> OTHER INFORMATION: Synthetic primer

<400> SEQUENCE: 14

```
gcgccgcact gcgccctgtc cgtaacg                                          27
```

<210> SEQ ID NO 15
<211> LENGTH: 27
<212> TYPE: DNA
<213> ORGANISM: Artificial Sequence
<220> FEATURE:
<223> OTHER INFORMATION: Synthetic primer

<400> SEQUENCE: 15

```
cgttacggac agggcgcagt gcggcgc                                          27
```

<210> SEQ ID NO 16
<211> LENGTH: 1053
<212> TYPE: DNA
<213> ORGANISM: Escherichia coli

<400> SEQUENCE: 16

```
atgaattatc agaacgacga tttacgcatc aaagaaatca agagttact tcctcctgtc       60
gcattgctgg aaaaattccc cgctactgaa aatgccgcga atacggttgc ccatgcccga     120
aaagcgatcc ataagatcct gaaaggtaat gatgatcgcc tgttggttgt gattggccca     180
tgctcaattc atgatcctgt gcggcaaaa gagtatgcca ctcgcttgct ggcgctgcgt     240
gaagagctga agatgagct ggaaatcgta atgcgcgtct attttgaaaa gccgcgtacc     300
acggtgggct ggaaagggct gattaacgat ccgcatatgg ataatagctt ccagatcaac     360
gacggtctgc gtatagcccg taaattgctg cttgatatta cgacagcgg tctgccagcg     420
gcaggtgagt ttctcgatat gatcacccca caatatctcg ctgacctgat gagctggggc     480
gcaattggcg cacgtaccac cgaatcgcag gtgcaccgcg aactggcatc agggctttct     540
tgtccggtcg gcttcaaaaa tggcaccgac ggtacgatta agtggcat cgatgccatt     600
aatgccgccg gtgcgccgca ctgcttcctg tccgtaacga aatgggggca ttcggcgatt     660
```

```
gtgaatacca gcggtaacgg cgattgccat atcattctgc gcggcggtaa agagcctaac      720
tacagcgcga agcacgttgc tgaagtgaaa gaagggctga acaaagcagg cctgccagca      780
caggtgatga tcgatttcag ccatgctaac tcgtccaaac aattcaaaaa gcagatggat      840
gtttgtgctg acgtttgcca gcagattgcc ggtggcgaaa aggccattat tggcgtgatg      900
gtggaaagcc atctggtgga aggcaatcag agcctcgaga gcggggagcc gctggcctac      960
ggtaagagca tcaccgatgc ctgcatcggc tgggaagata ccgatgctct gttacgtcaa     1020
ctggcgaatg cagtaaaagc gcgtcgcggg taa                                  1053
```

TRANSGENIC PLANTS HAVING ALTERED DAHP SYNTHASE ACTIVITY

RELATED APPLICATION DATA

This application is the U.S. National Stage of International Application No. PCT/IL2011/000535, filed Jul. 6, 2011, which claims the benefit of U.S. Provisional Application No. 61/361,549, filed Jul. 6, 2010, the contents of each of which are herein expressly incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 23,793 byte ASCII (text) file named "Seq_List" created on Jan. 4, 2013.

FIELD OF THE INVENTION

The present invention relates to means and methods for altering the activity of the 3-Deoxy-D-Arabino-Heptulosonate 7-Phosphate (DAHP) Synthase in plants leading to increased production of the Shikimate pathway derived primary and secondary metabolites, including aromatic amino acids.

BACKGROUND OF THE INVENTION

The shikimate pathway, present in many organisms including plants, links metabolism of carbohydrates to biosynthesis of aromatic compounds. In a sequence of several metabolic steps, primary carbon is converted via shikimate into chorismate, (upper part of FIG. 1). Chorismate then serves as a precursor for the synthesis of the three aromatic amino acids phenylalanine, tyrosine, and tryptophan (bottom part of FIG. 1). In plants, the products of the shikimate pathway itself as well as the aromatic amino acids produced downstream are involved in the production of multiple secondary metabolites, such as alkaloids, flavonoids, lignin, coumarins, indole derivatives and other phenolic compounds. Thus, the Shikimate pathway serves as a bridge between primary and secondary metabolism.

The first committed enzyme of the Shikimate pathway is 3-Deoxy-D-Arabino-Heptulosonate 7-Phosphate Synthase (DAHPS), which converts hosphoenolpyruvate (PEP) and Erythrose 4-Phosphate (E-4P) into 3-Deoxy-D-Arabino-Heptulosonate 7-Phosphate (DAHP) (FIG. 1). *Escherichia* (*E.*) *coli* has three different DAHPS isoenzymes encoded by the AroF, AroG and AroH genes, which encode proteins that are feedback inhibited by the individual aromatic amino acids tyrosine (Tyr) phenylalanine (Phe) and tryptophan (Trp), respectively (Brown, K. Genetics, 1968. 60(1):31-48). The major Phe-sensitive DAHPS isoform, which makes up to 80% of the total *E. coli* DAHPS activity, is a homotetramer protein encoded by the AroG gene (Hu, C. et al., J Basic Microbiol, 2003. 43(5): p. 399-406; Wallace, B. and J. Pittard, J Bacteriol, 1967. 93:237-244). It has also been suggested that the N-terminus as well as the interior regions of this AroG-encoded DAHPS are involved in its feedback inhibition by phenylalanine (Hu et al. 2003, supra; Xu, J. et al., J Basic Microbiol, 2004. 44(5):400-406: Ger, Y. et al., J Biochem, 1994. 116(5):986-990). Mutations replacing a number of amino acids in the AroG-encoded DAHPS, including proline at position 150 to leucine, leucie at position 175 to glutamine, leucine at position 179 to aspartic acid and phenylalanine at position 209 to alanine, significantly reduced the extent of feedback inhibition of 1 mM of phenylalnine while showing kinetic properties similar to the wild type (Xu et al. 2004, supra). These mutations were also associated with significant overproduction of phenylalanine in the bacterial cells (Hu et al. 2003, supra).

European Patent No. 1270721 discloses recombinant DNA sequences encoding feedback inhibition released enzymes, particularly a mutated AroG gene encoding 3-deoxy-D-arabinoheptulonic acid-7-phosphate synthase, wherein the proline residue 150 is substituted by a leucine residue, plasmids containing these recombinant DNA sequences, microorganisms transformed with these plasmids, and a process for preparing L-tryptophan, L-phenylalanine and L-tyrosine by fermentation.

In contrast to *E. coli* and many other bacterial species, the allosteric regulation of plant DAHPS is still questionable. (Gilchrist, D. and T. Kosuge, In: B. N. Miflin, ed, the Biochemistry of Plants, Academic Press, New York, 1980. 5:507-531; Herrmann, K. M. and L. M. Weaver, Annu Rev Plant Physiol Plant Mol Biol, 1999. 50:473-503). It has been described that the in vitro activities of DAHPS from different plant species may be weakly inhibited by Trp and Tyr or weakly activated by either Trp or Tyr. In addition, the activity of the bean (Vigna radiate) DAHPS is weakly inhibited by prephenate and arogenate, the precursors of Phe and Tyr biosynthesis. It is still unknown, however, whether this feedback is due to inhibition of the enzyme expression or inhibition of its activity.

*Arabidopsis* plants possess two DAHPS genes, DHS1 (At4G39980) and DHS2 (At4G33510) in addition to one putative gene (At1g22410) with high similarity to DHS1. The expression of DHS1 in *Arabidopsis* is induced by physical wounding or by infiltration with pathogenic *Pseudomonas syringae* strains (Keith, B. et al., Proc Natl Acad Sci USA, 1991. 88(19):8821-8825). The presence of amino-terminal extensions characteristic of chloroplast transit peptides in the *Arabidopsis* proteins encoded by DHS1 and DHS2 supports the notion that both proteins are localized in the chloroplast. Tomato (*Solanum esculentum*) also contains two distinct DHAPS encoding genes that contain plastid transit peptides and are differentially expressed (Gorlach, J. et al., Plant Mol Biol, 1993. 23(4):707-16). Nevertheless, despite the available information on DAHPS expression and activity in plants, it is still unknown whether this enzyme serves as a major regulator of the flux through the Shikimate pathway and hence whether DAHPS is a key regulatory enzyme bridging between primary and secondary metabolism.

U.S. Pat. No. 5,906,925 discloses methods for increasing the yield of 3-deoxy-D-arabino-heptulosonate 7-phosphate (DAHP) in microorganisms through genetic alterations, particularly by overexpression of phosphoenol pyruvate synthase.

U.S. Pat. No. 6,911,331 discloses isolated nucleic acid fragment encoding a DAHP synthetase. The patent also discloses the construction of a chimeric gene encoding all or a portion of the DAHP synthetase, in sense or antisense orientation, wherein expression of the chimeric gene results in production of altered levels of the DAHP synthetase in a transformed host cell, including plant cell.

U.S. Pat. No. 5,776,736 discloses the enzymes 3-dehydroquinate synthase, shikimate kinase, 5-enolpyruvoyl-Shikimate-3-phosphate synthase and chorismate synthase as rate-limiting enzymes in the common pathway of aromatic amino acid biosynthesis in prokaryotes. Transforming prokaryotic cells with exogenous DNA sequences encoding these enzymes resulted in a significant increase in the end product production.

U.S. Pat. No. 7,790,431 discloses enzymes and enzymatic pathways for the pyruvate-based synthesis of shikimate or at least one intermediate thereto or derivative thereof. The patent also discloses nucleic acids encoding the enzymes, cells transformed therewith, and kits containing said enzymes, cells, or nucleic acid. A KDPGa1 aldolase is used to perform condensation of pyruvate with D-erythrose 4-phosphate to form 3-deoxy-D-arabino-heptulosonate-7-phosphate (DAHP); a 3-dehydroquinate synthase is used to convert the DAHP to 3-dehydroquinate (DHQ); DHQ dehydratase can then convert DHQ to the key shikimate intermediate, 3-dehydroshikimate.

International (PCT) Application Publication No. WO 2009/072118 to the inventors of the present invention discloses that transforming plant cells with polynucleotide(s) encoding feedback-insensitive chorismate mutase and prephenate dehydrates results in altered content of at least one of the aromatic amino acids phenylalanine, tyrosine and tryptophan. However, these enzymes are located downstream the Shikimate pathway, and thus the amount of available chorismate is a "bottle neck" dictating the maximum levels of aromatic acids that may be produced.

Thus, means for modulation of the Shikimate pathway in plants towards the production of increased rates of the aromatic amino acids phenylalanine, tyrosine and tryptophan is highly desired, as these amino acids are both essential components of protein synthesis and also serve as precursors for a wide range of secondary metabolites that are important for plant growth as well as for human nutrition and health.

SUMMARY OF THE INVENTION

The present invention now discloses that attenuating the feedback inhibition of 3-deoxy-D-arabino-heptulosonate-7-phosphate synthase (DHAPS), the first enzyme of the Shikimate pathway in plants, triggers the accumulation of the direct products of the Shikimate pathway and of the aromatic amino acid phenylalanine. Levels of tryptophan and tyrosine are also increased, albeit to somewhat lesser extent compared to the level of phenylalanine.

The present invention is based in part on the unexpected finding that expression in a plant cell of the *E. coli* mutant AroG gene, encoding DAHPS having reduced sensitivity to feedback inhibition by phenylalanine (also referred to herein as "feedback insensitive DAHPS"), resulted in overproduction of the aromatic amino acids phenylalanine, tryptophan and tyrosine. Without wishing to be bound by any specific theory or mechanism of action, the observed increase in the aromatic amino acid contents can be attributed to overproduction of shikimate and/or chorismate, which release the "bottle neck" in the production of chorismate-derived secondary metabolites as well as of phenylalanine, tryptophan and tyrosine. One advantage of the teachings of the present invention relies upon the regulation of one of the first rate-limiting enzymes in the Shikimate pathway, such that the amount of precursor metabolites is increased. Having elevated amounts of the precursor metabolites enable the production of secondary metabolites at elevated amounts.

Thus, according to one aspect, the present invention provides a transgenic plant comprising at least one plant cell comprising an exogenous polynucleotide encoding 3-deoxy-D-arabino-heptulosonate-7-phosphate synthase (DAHPS) having a reduced sensitivity to feedback inhibition, wherein the transgenic plant comprises an increased amount of at least one of an aromatic amino acid, shikimate, chorismate or a catabolic product thereof compared to a corresponding non transgenic plant.

According to certain embodiments, the transgenic plant comprises an increased amount of at least one aromatic amino acid selected from the group consisting of phenylalanine, tyrosine, tryptophan or a combination thereof compared to a corresponding non transgenic plant.

According to other embodiments, the transgenic plant comprises an increased amount of phenylalanine compared to a corresponding non transgenic plant. According to further embodiments, the transgenic plant comprises an increased amount of tyrosine compared to a corresponding non transgenic plant. According to yet further embodiments, the transgenic plant comprises an increased amount of tryptophan compared to a corresponding non transgenic plant. According to additional embodiments, the transgenic plant comprises an increase amount of prephenate compared to a corresponding non transgenic plant.

According to other embodiments, the transgenic plant comprises an increased amount of at least one catabolic product of the aromatic amino acids compared to the corresponding non transgenic plant. According to certain embodiment, the catabolic product is a phenylpropanoid selected from the group consisting of lignin, chlorogenic acid (3-Caffeoylquinate), flavonoid and benzeniod.

According to yet further embodiments, the transgenic plant comprises an increased amount of shikimate, or catabolic products thereof compared to a corresponding non transgenic plant.

According to certain embodiments, the polynucleotide encodes a bacterial DAHPS. According to certain typical embodiments, the polynucleotide encodes *E. coli* DAHPS isoenzyme. According to certain currently typical embodiments, the polynucleotide encodes *E. coli* AroG DAHPS having a reduced sensitivity to feedback inhibition by phenylalanine.

According to certain embodiments, the feedback insensitive *E. coli* AroG DAHPS has at least one point mutation at a position selected from the group consisting of position 150, 175, 179 and 209 of the wild type *E. coli* AroG DAHPS, having the amino acid sequence set forth in SEQ ID NO:1 (NCBI accession number AAA23492).

According to certain embodiments, proline at position 150 is replaced by leucine (P150L). According to other embodiments, the leucine at position 175 is replaced by glutamine (L175Q). According to further embodiments, leucine at position 179 is replaced by aspartate (L179D). According to yet additional embodiments the phenylalanine at position 209 is replaced by alanine (F209A).

According to certain currently typical embodiments, the AroG DAHPS enzyme has a reduced sensitivity to feedback inhibition by phenylalanine, and the polynucleotide is selected from a polynucleotide encoding AroG DAHPS having the mutation L175Q (designated hereinafter $AroG_{175}$) having the amino acid sequence set forth in SEQ ID NO:2 and a polynucleotide encoding AroG DAHPS having the mutation F209A (designated hereinafter $AroG_{209}$) having the amino acid sequence set forth in SEQ ID NO:4. According to these embodiments, the polynucleotide is selected from the group consisting of a polynucleotide comprising the nucleic acid sequence set forth in SEQ ID NO:3 and a polynucleotide comprising the nucleic acid sequence set forth in SEQ ID NO:5.

The inventors of the present invention have previously disclosed that a significant portion of the synthesis of phenylalanine products in a plant cell occurs within the cell plastids. Thus, according to certain embodiments, the polynucleotides encoding the feedback insensitive AroG DAHPS further comprises a nucleic acid sequence encoding a plastid transit peptide. According to these embodiments, the polynucleotide encoding the plastid transit peptide comprises a nucleic acid sequence as set forth in SEQ ID NO:6. Typically, the polynucleotides are so designed that the encoded plastid transit peptide is fused at the amino terminus of the encoded polypeptide.

According to yet other embodiments, the polynucleotides of the present invention are incorporated in a DNA construct enabling their expression in the plant cell. According to one embodiment, the DNA construct comprises at least one expression regulating element selected from the group consisting of a promoter, an enhancer, an origin of replication, a transcription termination sequence, a polyadenylation signal and the like.

According to some embodiments, the DNA construct comprises a promoter. The promoter can be constitutive, induced or tissue specific promoter as is known in the art. According to typical embodiments, the promoter is a constitutive promoter operable in a plant cell. According to another embodiment, the DNA construct further comprises transcription termination and polyadenylation sequence signals.

Optionally, the DNA construct further comprises a nucleic acid sequence encoding a detection marker enabling a convenient detection of the recombinant polypeptides expressed by the plant cell. According to certain embodiments, the DNA construct further comprises a nucleic acid sequence encoding three repeats of hemagglutinin (HA) epitope tag. This epitope allows the detection of the recombinant polypeptide by using antibodies raised against the HA epitope tag, said tag having the nucleic acid sequence set forth in SEQ ID NO:7. According to one embodiment, the DNA construct comprises a nucleic acid sequence encoding a polypeptide containing the pea rbcS3 plastid transit peptide, L175Q AroG DAHPS and three repeats of the HA epitope tag, said polypeptide having SEQ ID NO:8. According to another embodiment, the DNA construct comprises a nucleic acid sequence encoding a polypeptide containing the pea rbcS3 plastid transit peptide, F209A AroG DAHPS and three repeats of the HA epitope tag, said polypeptide having SEQ ID NO:9.

The polynucleotides of the present invention and/or the DNA constructs comprising same can be incorporated into a plant transformation vector.

It is to be understood explicitly that the scope of the present invention encompasses homologs, analogs, variants and derivatives, including shorter and longer polypeptides, proteins and polynucleotides, as well as polypeptide, protein and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these variants and modifications must preserve the DAHPS activity of the polypeptide in the context of the present invention, that is activity which is not sensitive to feedback inhibition and thus leading to accumulation of shikimate-derived and chorismate-derived metabolites as disclosed herein. Specifically, any active fragments of the active polypeptide or protein as well as extensions, conjugates and mixtures are disclosed according to the principles of the present invention.

The present invention also encompasses seeds of the transgenic plant, wherein plants grown from said seeds comprise at least one cell having an altered content of at least one an aromatic amino acid, shikimate, chorismate or catabolic product thereof compared to plants grown from seeds of corresponding non transgenic plant. The present invention further encompasses fruit, leaves or any part of the transgenic plant, as well as tissue cultures derived thereof and plants regenerated therefrom.

According to yet another aspect, the present invention provides a method of inducing the synthesis of at least one of shikimate, chorismate and an aromatic amino acid in a plant, comprising (a) transforming at least one plant cell with an exogenous polynucleotide encoding DAHPS having reduced sensitivity to feedback inhibition and (b) regenerating the at least one transformed cell into a transgenic plant comprising at least one cell having an increased amount of at least one of shikimate, chorismate, an aromatic amino acid and secondary metabolites derived therefrom, compared to a corresponding cell of a non transgenic plant.

According to certain embodiments, the DAHPS has reduced sensitivity to feedback inhibition by phenylalanine. According to other embodiment, the polynucleotide encodes a mutant DAHPS selected from the group consisting of L175Q AroG DAHPS and F209A AroG DAHPS.

The exogenous polynucleotide(s) encoding L175Q or F209A AroG DAHPS according to the teachings of the present invention can be introduced into a DNA construct to include the entire elements necessary for transcription and translation as described above, such that the polypeptides are expressed within the plant cell.

Transformation of plants with a polynucleotide or a DNA construct may be performed by various means, as is known to one skilled in the art. Common methods are exemplified by, but are not restricted to, *Agrobacterium*-mediated transformation, microprojectile bombardment, pollen mediated transfer, plant RNA virus mediated transformation, liposome mediated transformation, direct gene transfer (e.g. by microinjection) and electroporation of compact embryogenic calli. According to one embodiment, the transgenic plants of the present invention are produced using *Agrobacterium* mediated transformation.

Transgenic plants comprising the polynucleotides of the present invention may be selected employing standard methods of molecular genetics, as are known to a person of ordinary skill in the art. According to certain embodiments, the transgenic plants are selected according to their resistance to an antibiotic. According to one embodiment, the antibiotic serving as a selectable marker is one of the group consisting of Cefotaxime, Vancomycin and Kanamycin. According to other embodiments, the transgenic plants are selected according to their resistance to an herbicide. According to one embodiment, the herbicide is Glufosinate ammonium (Basta).

According to other aspects the present invention relates to the transgenic plants generated by the methods of the present invention as well as to their seeds, fruit, roots and other organs or isolated parts thereof.

Any plant can be transformed with the polynucleotides of the present invention to produce the transgenic plants having elevated amount of at least one of shikimate, chorismate, an aromatic amino acid and secondary metabolites derived therefrom, compared to the non-transgenic plant. According to certain embodiments, the plant is a crop plant. According to certain typical embodiments, the plant is a tomato plant.

Other objects, features and advantages of the present invention will become clear from the following description and drawings.

BRIEF DESCRIPTION OF THE DRAWINGS

FIG. 2 shows expression of the bacterial AroG gene in transgenic *Arabidopsis*. FIG. 2A -FIG. 2C show schematic diagrams of the chimeric AroG genes. 35S:PRO-Ω: cauliflower mosaic virus 35S promoter fused to Ωtranslation enhancer or E8: a ripening and ethylene regulatory regions in a fruit-specific promoter from tomato (*Lycopersicon esculentum*); TP: plastid transit peptide; AroG: the bacterial DAHPS including (A) WT (original sequence), (B) mutant variant in amino acid located at 175 position and (C) mutant variant in amino acid located at 209 position; HA, three copies of the hemagglutinin epitope tag; OCS: octopine synthase terminator.

FIG. 8 shows metabolic characterization of transgenic tomato plants expressing a bacterial feedback insensitive AroG enzyme. Samples of T1 generation ripe tomato fruit were collected, extracted and analyzed using the LC-MS platform. The independent transgenic genotypes are: AroG175-6, AroG175-11, AroG209-4, AroG209-8, AroG209-9 and wild-type (WT). FIG. 8A: PCA plot of datasets was obtained from 3,094 mass signals in negative ion mode. Each data point represents an independent sample (4-5 repeats). The first two dimension variances are given in this panel. FIG. 8B: Relative level of Phe, Trp and Tyr. Asterisks indicated statistically significant differences between the AroG genotypes and the WT, using the Student's t-test. Bars on top of the histograms indicate standard errors.

FIG. 9 shows the metabolite profiles of developing tomato fruit expressing $AroG_{209-9}$ gene and wild-type (WT). FIG. 9A: PCA plot of metabolic profiles obtained by GC-MS analysis (125 detected metabolites). FIG. 9B: PCA plots of metabolic profiles obtained by UPLC-qTOF-MS analysis. The fruit were sampled on three developing stages: mature green (MG; ~42 days post anthesis (DPA)); breaker (Br; ~44 DPA) and red (red; ~48 DPA) and separated to peel and flesh (n=5-6).

DETAILED DESCRIPTION OF THE INVENTION

Figure 1:
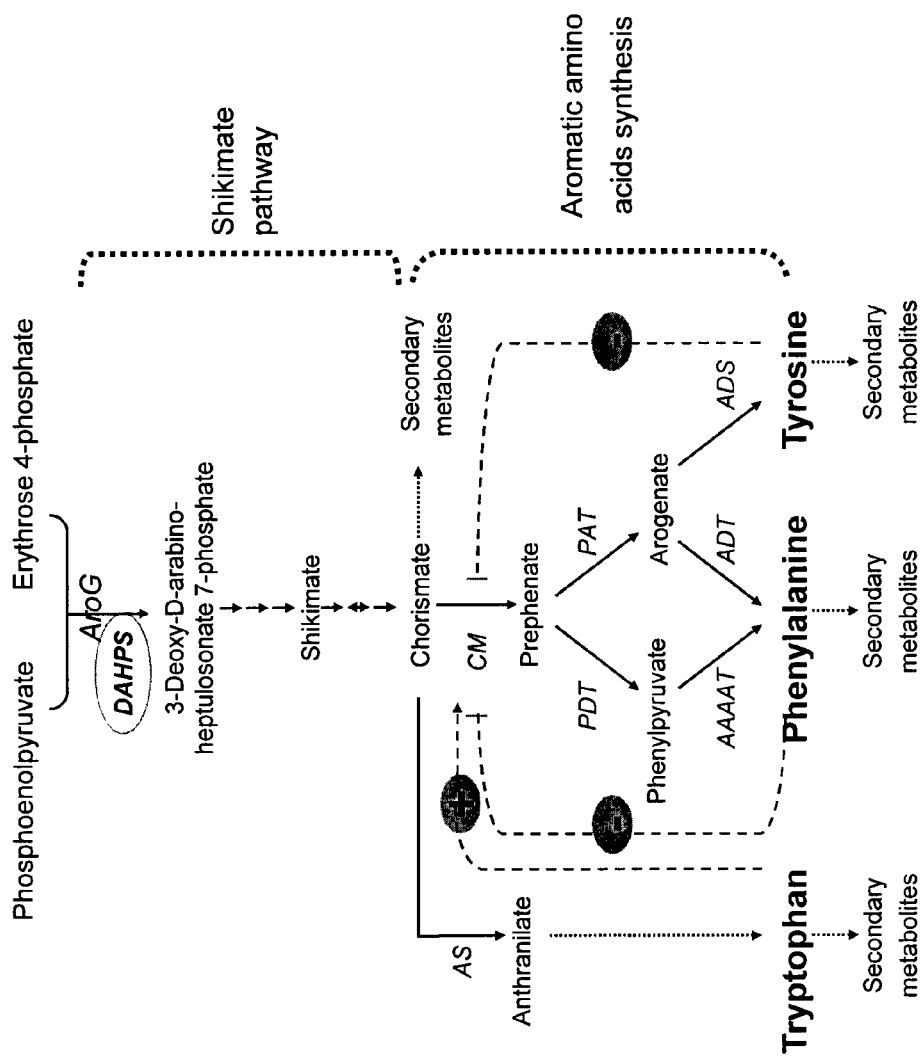
FIG. 1 shows schematic diagram of the shikimate and aromatic amino acids metabolic network in plants. A continuous arrow represents a one step enzymatic reaction and a series of arrow represents reactions of several enzymatic steps. Dashed grey lines with a minus or plus signs represent feedback inhibition and activation loops, respectively. Abbreviations: DAHPS, 3-deoxy-d-arabino-2-heptulosonate 7-phosphate synthase; AS, anthranilate synthase; CM, chorismate mutase; PDT, prephanate dehydratase; PAT, prephanate aminotransferase; AAAAT, aromatic amino acid aminotransferase; ADT, arogenate dehydratase and ADS, arogenate dehydroganse.

The present invention discloses transgenic plants transformed with exogenous nucleic acid encoding 3-deoxy-d-arabino-heptulosonate-7-phosphate synthase (DAHPS) having a reduced sensitivity to feedback inhibition by a product of its activity, the aromatic amino acid phenylalanine, compared to a wild type DAHPS. The present invention shows for the first time that releasing this feedback inhibition in a plant cell results in increased accumulation of shikimate and the aromatic amino acids phenylalanine, tyrosine and tryptophan. Furthermore, the present invention now shows that expression of the feedback-insensitive DAHPS triggers the expression of genes associated with biotic stress, including pathogenesis-related genes, as well as genes associated with cell wall metabolism, secondary metabolism, biotic-stress related hormone metabolism (ethylene as well as salicylic acid that is produced via the Shikimate and Phenylalanine biosynthesis pathways), redox state regulation, transcription factors and signaling genes.

The present invention now shows that transgenic plants expressing the feedback-insensitive DAHPS gene produce increased amount of phenylalanine compared to corresponding non transgenic plants. Moreover, the present invention now shows that the expression of a bacterial DAHPS polypeptide having reduced sensitivity to feedback inhibition in transgenic plants, particularly within the plastid of the plant cell leads to over production of secondary metabolites, which require phenylalanine and/or tyrosine and/or tryptophan and/or intermediate compounds produced through the phenylalanine pathway for their biosynthesis. Particularly, the second metabolites include phenylpropanoids selected from the group consisting of lignin, which is an essential component of the cell wall; chlorogenic acid (3-Caffeoylquinate), an antioxidant and inhibitor of the tumor promoting activity of phorbol esters; and flavonoids, which are plant pigment contributing to plant coloring and UV protection. The alteration of the Shikimate pathway may also lead to the production of phenylpropanoids class of benzeniods, which are volatile compounds essential for sweet, floral and fruity flavors.

The present invention also provides a method of producing transgenic plants having increased amounts of at least one of shikimate, chorismate and an aromatic amino acid selected from the group consisting of phenylalanine, tryptophan and tyrosine as compared to a corresponding non transgenic plant. Also provided by the present invention are plant cells, comprising exogenous nucleic acids encoding DAHPS that is insensitive to feedback inhibition, particularly to feedback inhibition by phenylalanine, and plant seeds and progenies obtained from the transgenic plants.

The present invention makes a significant contribution to the art by providing new strategies to engineer plants having the capability to modify the production of secondary metabolites. The present invention utilizes primary enzymes in the Shikimate pathway, not previously shown to be manipulated in plants by the release of feedback inhibition, for overproduction of shikimate and aromatic amino acids as well as secondary metabolites derived therefrom.

The plants of the present invention are capable of overproducing secondary metabolites that have beneficial effects on the plant characteristics, for example fruit taste and aroma. Furthermore, the plants of the invention overproduce secondary metabolites required for their beneficial characterizations, which are naturally produced by the plant in insufficient amounts to be used commercially.

Definitions

As used herein, the terms "having reduced sensitivity to feedback inhibition", "insensitive to feedback inhibition" or "feedback insensitive" with regard to DAHPS activity refer to complete or essential relieve of feedback inhibition at 1 mM of Phe, while showing similar specific enzymatic activity as the wild type (Hu et al. 2003, supra).

The term "plant" is used herein in its broadest sense. It includes, but is not limited to, any species of woody, herbaceous, perennial or annual plant. It also refers to a plurality of plant cells that are largely differentiated into a structure that is present at any stage of a plant's development. Such structures include, but are not limited to, a root, stem, shoot, leaf, flower, petal, fruit, etc.

As used herein, the term "feedback inhibition" refers to a cellular control mechanism of enzyme activity, in which an enzyme that catalyzes the production of a particular substance in the cell is inhibited when that substance has accumulated to a certain level.

The term "phenylalanine catabolic product(s)" refers to classes of plant-derived organic compounds that are biosynthesized from the amino acid phenylalanine, particularly phenylpropanoids. The phenylpropanoids have a wide variety of functions in the plant, including defense against herbivores, microbial attack, or other sources of injury; as structural components of cell walls; as protection from ultraviolet light; as pigments; and as signaling molecules.

The term "3-Deoxy-D-Arabino-Heptulosonate 7-Phosphate Synthase (DAHPS)" as used herein refers to a protein having the enzymatic activity of converting Phosphoenolpyruvate (PEP) and Erythrose 4-Phosphate (E-4P) into 3-Deoxy-d-Arabino-Heptulosonate 7-Phosphate (DAHP) (FIG. 1).

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

The terms "polynucleotide", "polynucleotide sequence", "nucleic acid sequence", and "isolated polynucleotide" are used interchangeably herein. These terms encompass nucleotide sequences and the like. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids.

An "isolated" nucleic acid molecule is one that is substantially separated from other nucleic acid molecules which are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated. A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

The term "recombinant" refers to an artificial combination of two otherwise separated segments of sequence, e.g., by chemical synthesis or by the manipulation of isolated segments of nucleic acids by genetic engineering techniques.

The term "construct" as used herein refers to an artificially assembled or isolated nucleic acid molecule which includes the gene of interest. In general a construct may include the gene or genes of interest, a marker gene which in some cases can also be the gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters which cause a gene to be expressed in most cell types at most times are commonly referred to as "constitutive promoters". New promoters of various types useful in plant cells are constantly being discovered; numerous examples may be found in Okamuro J K and Goldberg R B (1989) Biochemistry of Plants 15:1-82.

As used herein, the term an "enhancer" refers to a DNA sequence which can stimulate promoter activity, and may be an innate element of the promoter or a heterologous element inserted to enhance the level or tissue-specificity of a promoter.

The term "expression", as used herein, refers to the production of a functional end-product e.g., an mRNA or a protein.

The term "transgenic" when used in reference to a plant or seed (i.e., a "transgenic plant" or a "transgenic seed") refers to a plant or seed that contains at least one heterologous transcribeable polynucleotide in one or more of its cells. The term "transgenic plant material" refers broadly to a plant, a plant structure, a plant tissue, a plant seed or a plant cell that contains at least one heterologous polynucleotide in at least one of its cells. A "transgenic plant" and a "corresponding non transgenic plant" as used herein refer to a plant comprising at least one cell comprising a heterologous transcribeable polynucleotide and to a plant of the same type lacking said heterologous transcribeable.

The terms "transformants" or "transformed cells" include the primary transformed cell and cultures derived from that cell regardless to the number of transfers. All progeny may not be precisely identical in DNA content, due to deliberate or inadvertent mutations. Mutant progeny that have the same functionality as screened for in the originally transformed cell are included in the definition of transformants.

Transformation of a cell may be stable or transient. The term "transient transformation" or "transiently transformed" refers to the introduction of one or more exogenous polynucleotides into a cell in the absence of integration of the exogenous polynucleotide into the host cell's genome. Transient transformation may be detected by, for example, enzyme-linked immunosorbent assay (ELISA), which detects the presence of a polypeptide encoded by one or more of the exogenous polynucleotides. Alternatively, transient transformation may be detected by detecting the activity of the protein (e.g. β-glucuronidase) encoded by the exogenous polynucleotide.

The term "transient transformant" refers to a cell which has transiently incorporated one or more exogenous polynucleotides. In contrast, the term "stable transformation" or "stably transformed" refers to the introduction and integration of one or more exogenous polynucleotides into the genome of a cell. Stable transformation of a cell may be detected by Southern blot hybridization of genomic DNA of the cell with nucleic acid sequences which are capable of binding to one or more of the exogenous polynucleotides. Alternatively, stable transformation of a cell may also be detected by enzyme activity of an integrated gene in growing tissue or by the polymerase chain reaction of genomic DNA of the cell to amplify exogenous polynucleotide sequences.

The term "stable transformant" refers to a cell which has stably integrated one or more exogenous polynucleotides into the genomic or organellar DNA. It is to be understood that a plant or a plant cell transformed with the nucleic acids, constructs and/or vectors of the present invention can be transiently as well as stably transformed. The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

According to one aspect, the present invention provides a transgenic plant comprising at least one plant cell comprising an exogenous polynucleotide encoding 3-deoxy-D-arabino-heptulosonate-7-phosphate synthase (DAHPS) having reduced sensitivity to feedback inhibition, wherein the transgenic plant comprises an increased amount of at least one of an aromatic amino acid, shikimate, chorismate or a catabolic product thereof compared to a corresponding non transgenic plant.

According to certain embodiments, the polynucleotide encodes a bacterial DAHPS. According to certain typical embodiments, the polynucleotide encodes feedback insensitive E. coli DAHPS isoenzyme. According to further currently typical embodiments, the polynucleotide comprises E. coli AroG gene encoding a DAHPS having a reduced sensitivity to feedback inhibition.

According to certain embodiments, the E. coli AroG gene encoding the feedback insensitive DAHPS has at least one point mutation at a position selected from the group consisting of position 150, 175, 179 and 209 of the wild type E. coli AroG DAHPS, having the amino acid sequence set forth in SEQ ID NO:1. According to one embodiment, proline at position 150 is replaced by leucine (P150L). According to other embodiments, the leucine at position 175 is replaced by glutamine (L175Q). According to further embodiments, leucine at position 179 is replaced by aspartic acid (L179D). According to yet additional embodiments the phenylalanine at position 209 is replaced by alanine (F209A).

According to certain currently preferred embodiments, the AroG gene encodes a DAHPS that shows reduced sensitivity to feedback inhibition by phenylalanine. According to these embodiments, the polynucleotide encodes DAHPS having the mutation L175Q (designated hereinafter $AroG_{175}$). According to one embodiment, the feedback insensitive DAHPS has an amino acid sequence as set forth in SEQ ID NO:2.

According to other currently preferred embodiments, the AroG gene encodes a DAHPS that is insensitive to feedback inhibition by phenylalanine. According to these embodiments, the polynucleotide encodes DAHPS having the mutation F209A (designated hereinafter $AroG_{209}$). According to one embodiment, the feedback insensitive DAHPS has an amino acid sequence as set forth in SEQ ID NO:4.

According to other currently typical embodiments, the AroG polynucleotide comprises the nucleic acid sequence set forth in any one of SEQ ID NO:3 and SEQ ID NO:5.

Despite the major importance of the aromatic amino acid metabolism in plant primary and secondary production, still very little is known about the regulation of the conversion of primary carbon and nitrogen metabolites via the Shikimate pathway into the biosynthesis of the three aromatic amino acids phenylalanine, tyrosine and tryptophan.

Figure 7:
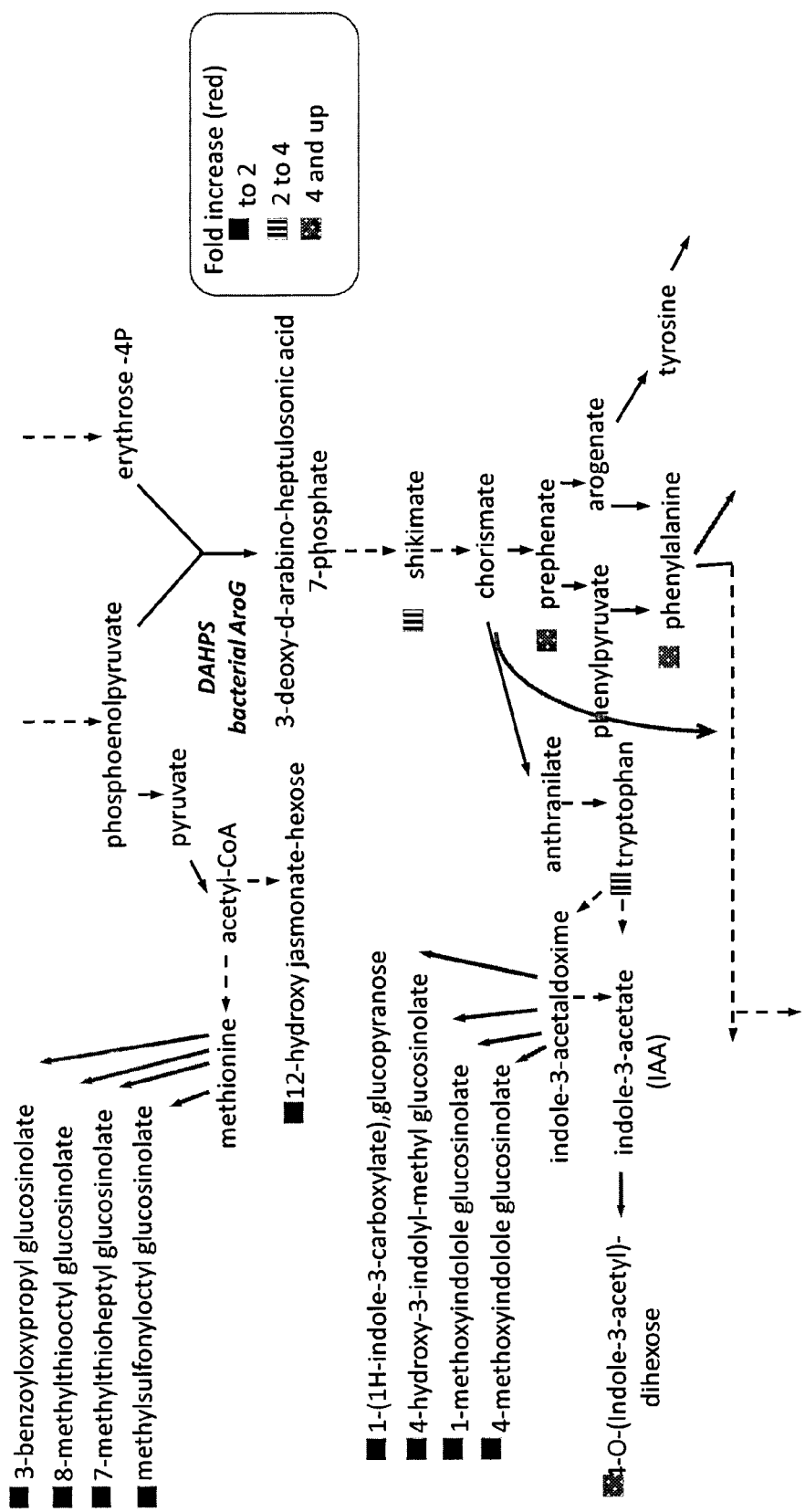
FIG. 7 shows a metabolic map describing the changes in the levels of specific metabolites in *Arabidopsis* plants expressing the $AroG_{175}$ gene compared to the control. Metabolites whose levels increased are marked in small squares having different patterns, as indicated in the figure. The broken arrows represent several consecutive enzymatic steps. The black and gray arrows represent known and unknown enzymatic steps, respectively.
Figure 7:
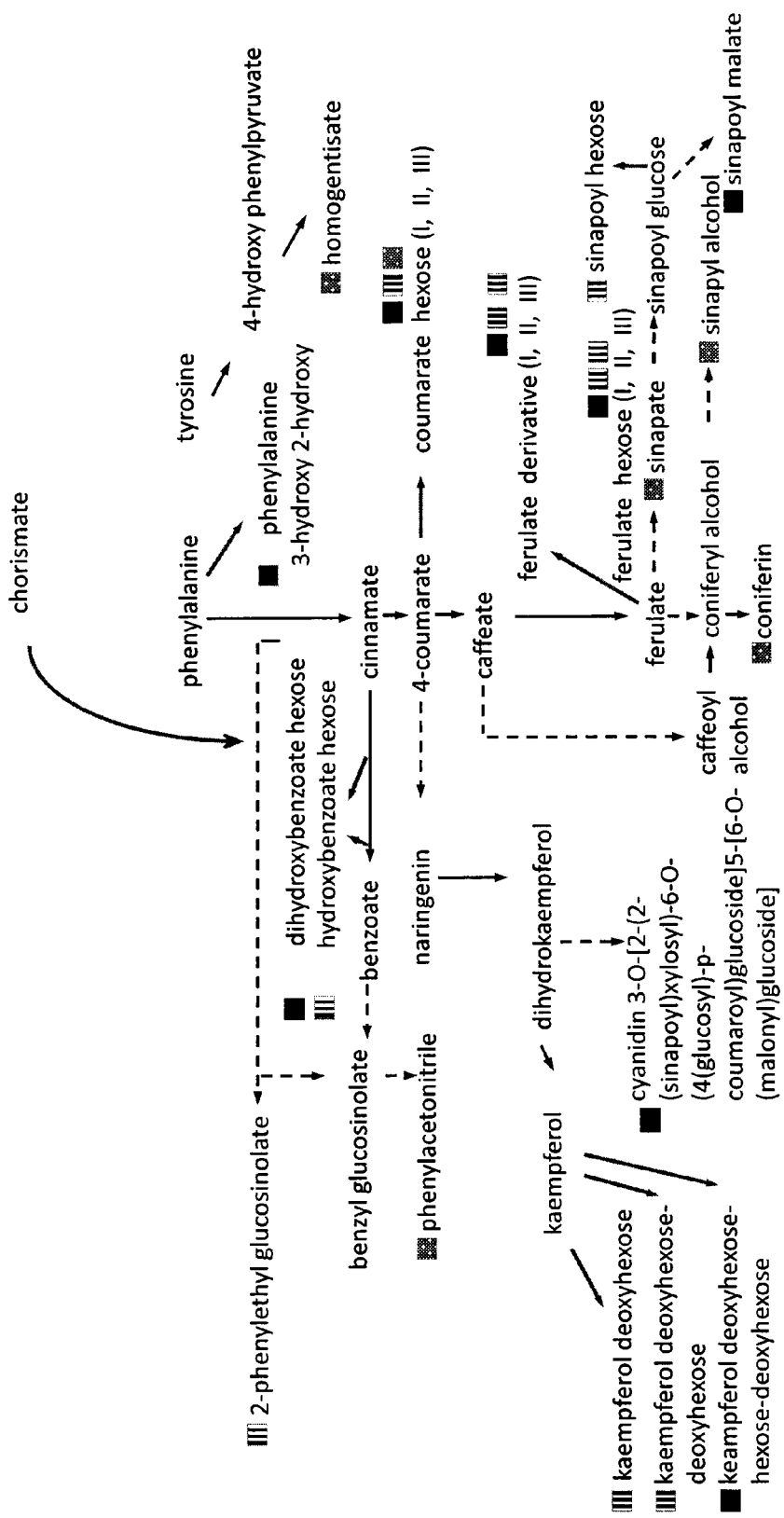

The present invention now shows that *Arabidopsis* and tomato plants expressing the $AroG_{175}$ or $AroG_{209}$ have enhanced levels of the three aromatic amino acids phenylalanine, tyrosine and tryptophan. In *Arabidopsis*, the levels of phenylalanine and tryptophan were found to be elevated more significantly, while in tomato the increase in the levels of phenylalanine and tyrosine was more prominent. This finding implies that DAHPS is a limiting enzyme that its activity regulates the conversion of primary carbon metabolites via the conversion of chorismate to aromatic amino acids as well as to metabolites that are derived directly from chorismate. Interestingly, among the two aromatic amino acids, phenylalanine accumulation was stimulated to a much higher degree than tryptophan in the $AroGj_{75}$ expressing *Arabidopsis* plants (FIG. 5). These results are concomitant with previous studies of carbon consumption suggesting that approximately 30% of the carbon fixed in photosynthesis is directed to the phenylalanine branch and toward lignin biosynthesis while the flux towards the tyrosine branch being far smaller (Rippert P. and M. Matringe, 2002. European Journal of Biochemistry 269(19):4753-4761; Pribat A. et al., 2010. Plant cell 22(10):3410-22). Without wishing to be bound by any specific theory or mechanism of action these results suggest that under favorable (non-stress) growth conditions the phenylalanine biosynthesis pathway efficiently competes with the tryptophan biosynthesis pathway over their common precursor metabolite chorismate (FIG. 7). The direction towards phenylalanine may be due to elevated expression and/or superior enzymatic activity of chorismate mutase leading to phenylalanine biosynthesis over the expression of athrenilate synthase leading to tryptophan biosynthesis (FIG. 1).

According to certain embodiments, the transgenic plant comprises an increased amount of at least one aromatic amino acid selected from the group consisting of phenylalanine, tyrosine, tryptophan or a combination thereof compared to a corresponding non transgenic plant. It is to be explicitly understood that each possibility represents a separate embodiment of the present invention.

According to other embodiments, the transgenic plant comprises an increased amount of at least one catabolic product of phenylalanine compared to the corresponding non transgenic plant. According to certain embodiments, the catabolic product of phenylalanine is selected from several classes of metabolites including, but not limited to: terpenoids; glycoalkalodies (dehydrolycoperoside G, F or A); carotenoids (phytoene, phytofluene or lycopene); phenylpropanoids; lignin (caffeate, ferulate); coumarate and caffeoylquinate; flavonoids (Kaempferol, Quercetin derivatives and anthocyanins); phenylalanine derived glucosinolate (2-phenylethyl glucosinolate and phenylacetonitrile); and salicylate derivatives (hydroxybenzoate hexose and dihydroxybenzoate hexose). According to one embodiment, the catabolic product of tyrosine is homogentisate. According to one embodiment, the catabolic product of tryptophan is selected from several classes of metabolites selected from, but not limited to: tryptophan derived glucosinolates (1-(1H-indole-3-carboxylate) glucopyranose, 4-hydroxy-indolyl-3-methyl glucosinolate, 4-methoxyindole glucosinolate, 1-methoxyindole glucosinolate, 4-O-(Indole-3-acetyl)-dihexose); Auxin conjugates (4-O-(Indole-3-acetyl)-dihexose). The present invention further shows that the amount of additional classes of metabolites is elevated in the transgenic plant compared to a corresponding non-transgenic plant, including, but not limited to: monosaccharide (mannose, fructose, guanosine, fructose-6-phosphate); oligosaccharide (maltose, raffinose, trehalose and cellobiose); additional amino acids (glycine, glutamine, threonine, aspargine); polyamines (Putrecine); jasmonate conjugates (12-hydroxy jasmonate-hexose); methionine derived glucosinolates (3-benzoyloxypropyl glucosinolate, 8-methylthiooctyl glucosinolate, 7-methylthioheptyl glucosinolate and methylsulfonyloctyl glucosinolate); and combinations thereof.

The present invention further shows that $AroG_{175}$ expression triggers a significant increase in the accumulation of shikimate as well as of prephenate, the precursor of phenylalanine biosynthesis (FIG. 1, FIG. 4 and FIG. 5A-B). Without wishing to be bound by any specific theory or mechanism of action, these results suggest that the enzymatic steps involving shikimate kinase and prephenate aminotransferase, converting the metabolites shikimate and prephenate to their respective downstream metabolites shikimate-3-phosphate and arogenate/phenylpyruvate represent novel bottleneck regulatory enzymes of the Shikimate and aromatic amino acid biosynthesis pathways.

In *Arabidopsis*, AroG$_{175}$ expression increased the levels of a number of phenylalanine-derived secondary metabolites, including lignin precursors and their derivatives, anthocyanins, flavonoids, phenylalanine-derived glucosinolates, tryptophan derived glucosinolate, Methionine derived glucosinolates, Auxin, jasmonate and salicylate conjugates (FIGS. 5, 7). Salicylate can be synthesized from chorismate or cinnamate or benzoate and its conjugates include several glucosylated forms, such as salicyloyl glucose ester and salicyloyl glucoside. Altered production of phenylalanine-derived secondary metabolites was previously observed upon expression of a bacterial bi-functional PheA gene (International Application Publication No. WO2009/072118 to the inventors of the present invention).

Figure 10:
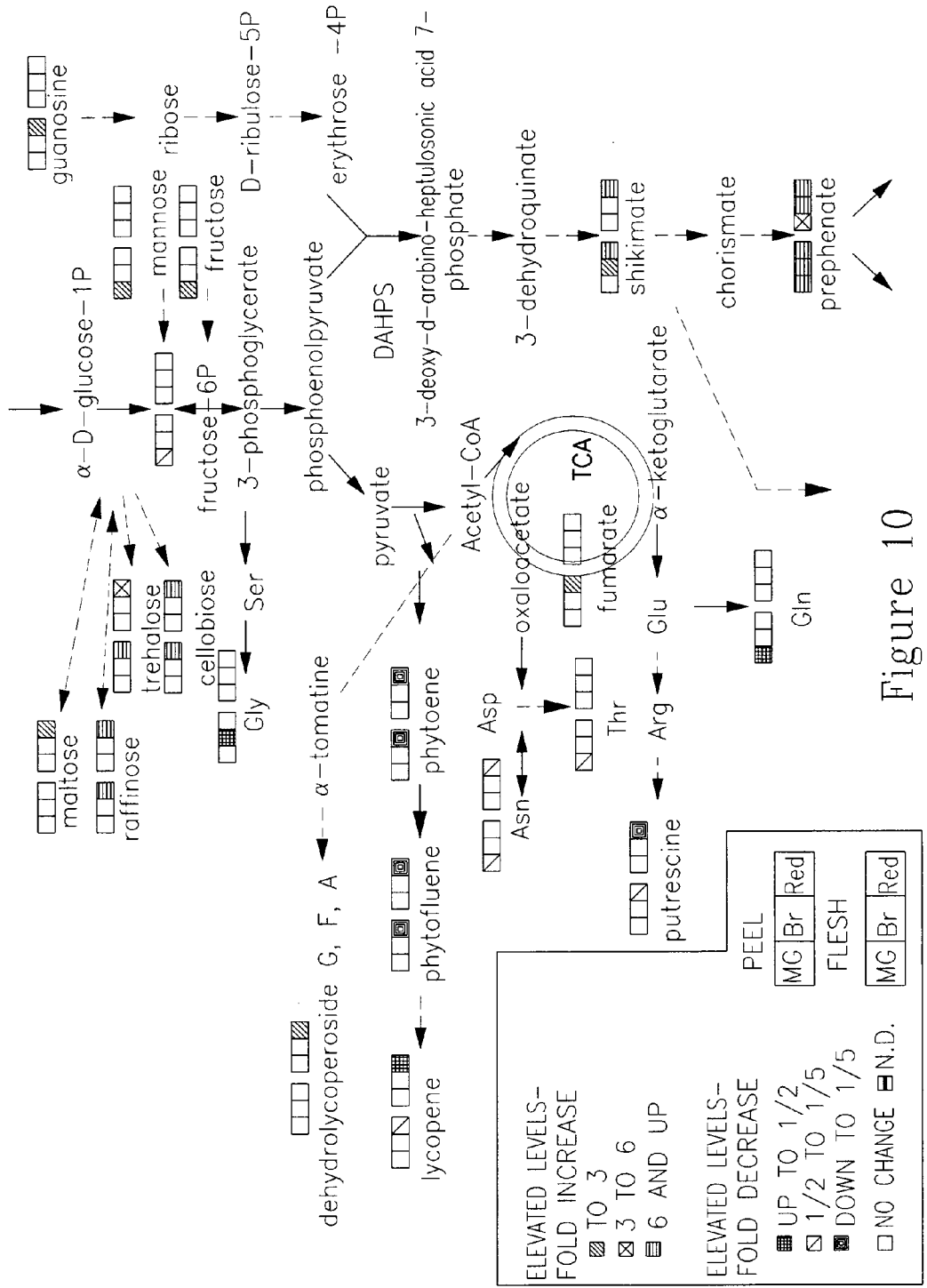
FIG. 10 shows a metabolic scheme summarizing the metabolic changes in tomato fruit expressing the $AroG_{209-9}$ gene. Metabolites that their levels significantly increased or decreased in the transgenic fruit (peel and flesh) compared to the control fruit are marked in two groups of three squares: first group regarding to the peel and second group regarding the flesh. The circles mark volatiles compounds, which were detected only in the red developing stage. The broken arrows represent several consecutive enzymatic steps.
Figure 10:
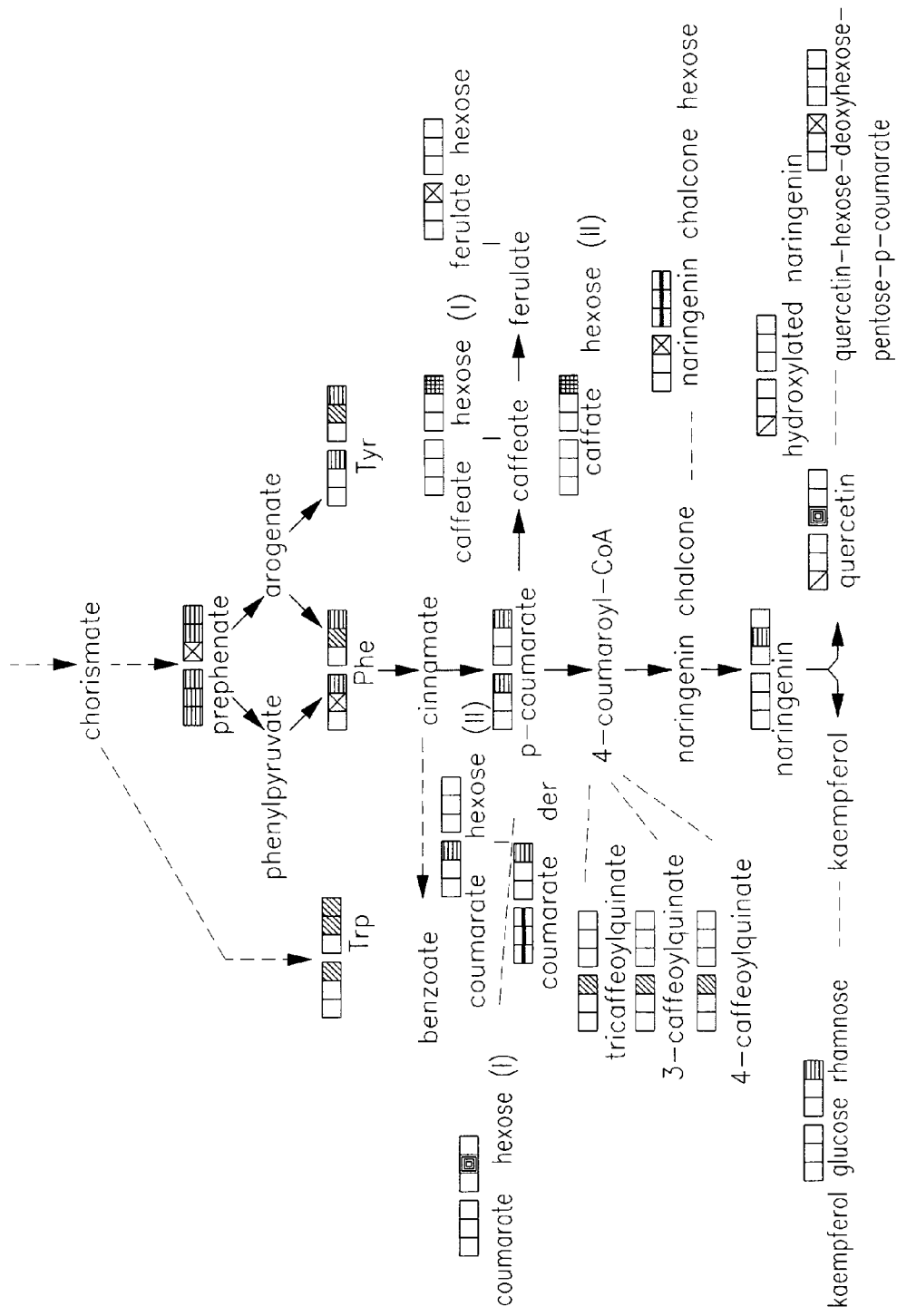

In tomato fruit, AroG$_{209}$ expression increased the levels of a number of phenylalanine-derived secondary metabolites including anthocyanins, flavonoids, coumarate and caffeoylquinate derivatives as well as monosaccharides and oligosaccharides (FIG. 10 and table 1).

Taken together, these results imply the presence of a regulatory cross interaction between the fluxes of the shikimate and aromatic amino acid biosynthesis pathways and their further metabolism into various secondary metabolites. The results also indicate that DAHPS functions as an important regulatory enzyme in the conversion of primary to secondary metabolism in plants. Manipulating the expression of combinations of genes, particularly chorismate mutase, (CM), prephenate dehydratase (PDT) and 3-Deoxy-D-Arabino-Heptulosonate 7-Phosphate Synthase (DAHPS), having reduced sensitivity to feedback inhibition by phenylalanine, may thus result in synergistic effect on the accumulation the aromatic amino acids phenylalanine and tyrosine and metabolites derived thereof.

As is shown in the Examples section hereinbelow, modulation of the DAHPS gene triggers significant expression changes in a moderate number of genes (109 genes). It appears that a considerable subset of these genes could be associated with biotic stresses, including those involved in hormone metabolism (cytokinin, absicisic acid, salicylate and jasmonate), several classes of transcription factors (TF) (MYBs, WRKYs and APETALA2/Ethylene-responsive element binding proteins), transportes, genes involved in signaling (calcium and cytokinin AAR-genes), genes encoding pathogenesis-related (PR) proteins including disease resistance proteins (TIR-NB proteins), and genes involved in redox regulation. These results are concomitant with the results of previous reports showing that pathogen attack and physical wounding stimulate the expression of the endogenous DAHPS genes in various plants, including *Arabidopsis* (Keith B. et al., 1991. Proceedings of the National Academy of Sciences 88(19):8821-8825), tomato (Gorlach J. et al., 1993. Plant Molecular Biology 23(4): 707-716) and potato (Muday G. K. and K. M. Herrmann, 1992. Plant Physiology 98(2): 496-500; Jones J. D. et al., 1995. Plant Physiology 108(4): 1413-1421). Additional studies also suggested that antisense inhibition of potato DAHPS transcript reduced the lignin content in the cell wall (Jones et al. 1995, supra).

The present invention shows that in the AroG$_{175}$ genotype, the change in the expression level of genes associated with synthesis of phenylalanine-derived secondary metabolites, including phenylpropanoids and metabolites associated with cell wall and salicylate metabolism correlated with changes in the levels of these classes of metabolites.

Particularly, the levels of indole-glucosinolates, aliphatic-glucosinolates and phenylalanine-glucosinolates were significantly increased in the AroG$_{175}$ lines in correlation to the increase in the mRNA levels of the following genes: (i) the gene encoding Flavin-Monooxygenase (FMO like glucosinolate s-oxygenase (AT1G65860; 2.1 fold increased) which catalyzes the conversion of methylthioalkyl glucosinolates to methylsulfinylalkyl glucosinolates and (ii) the gene encoding CYP81F2, a cytochrome P450 enzyme (AT5G57220; 2.7 fold increased), involved in indole glucosinolate metabolism. Without wishing to be bound by any specific theory or mechanism of action, the altered transcriptom and metabolome in AroG$_{175}$ transgenic plants supports a regulatory link between glucosinolate metabolism and the Shikimate pathway.

The expression level of 16 genes, categorized as genes associated with the circadian clock, was also induced in the AroG$_{175\text{-}2}$ transcriptome. These circadian clock-related genes included those encoding MYB transcription factors (At1G01060 and At2G46830) and Zinc Finger DNA-binding proteins that regulate gene expression (At2G31380 and At5G15850). Clusters of circadian-regulated genes were previously found to connect important signaling networks that coordinate plant growth with rhythmic changes in the environment, including auxin, phenylpropanoid biosynthesis and starch metabolism. In addition, by over expression of the PRODUCTION OF ANTHOCYANIN PIGMENT1 (PAP1) transcription factor, which regulates the expression of several genes encoding key flavonoid enzymes, it has been shown that these target genes are regulated by the circadian clock. The co-regulation of PAP1 with the phenylpropanoids biosynthesis genes has also suggested that PAP1 acts as a master regulator of clock-controlled transcription of these genes (Harmer S. L. et al., 2000. Science 290(5499): 2110-2113). Hence, the findings of the present invention support the presence of a novel regulatory link between the expression of genes controlling physiological processes that are associated with the circadian clock and the conversion of primary to secondary metabolites.

Another enriched gene category displaying increased expression was associated with nitrate assimilation, as it included genes encoding a nitrate transporter (At3g21670; NTP3) and two Nitrate Reductases (At1g77760; NIA1 and At1g37130; NIA2). The regulation of nitrogen metabolism is strongly associated with the regulation of glycolysis and the pentose phosphate pathway that serve as the donors of PEP and E-4P, the two substrates of DAHPS (Stitt M., 1999. Current Opinion in Plant Biology 2(3):178-186). In addition, nitrogen metabolism and translocation in plant cells has a major regulatory role in the competition between pathogens and their host plants for nitrogen availability. In the AroG$_{175}$ transcriptome, genes associated with nitrate assimilation and disease resistance, including genes encoding PR proteins were induced.

Without wishing to be bound by any specific theory or mechanism of action, the results of the present invention suggest that DAHPS activity, and perhaps the activity of other enzymes of the Shikimate pathway, influence the network connecting nitrogen metabolism with pathogen response in *Arabidopsis* plants.

Several genes putatively encoding transcription factors were down regulated in the AroG$_{175\text{-}2}$ line, including for example Zinc Finger B-box type proteins with a CCT domain (At3G07650, AT5G48250, At1G28050, At3G20810, At1G07050). The expression of three other genes, encoding proteins associated with the circadian clock cascade, were decreased, including TOC1 (Timing of CAB expression 1; At5G61380), Pseudo-response regulator (At5G60100) and ELF4 (Early flowering 4; At2G40080).

Producing the Transgenic Plants

Cloning of a polynucleotide encoding the AroG DAHPS can be performed by any method as is known to a person skilled in the art. Various DNA constructs may be used to express the AroG DAHPS in a desired plant.

The present invention provides a DNA construct or an expression vector comprising a polynucleotide encoding AroG DAHPS, which may further comprise regulatory elements, including, but not limited to, a promoter, an enhancer, and a termination signal.

Among the most commonly used promoters are the nopaline synthase (NOS) promoter (Ebert et al., 1987 Proc. Natl. Acad. Sci. U.S.A. 84:5745-5749), the octapine synthase (OCS) promoter, caulimovirus promoters such as the cauliflower mosaic virus (CaMV) 19S promoter (Lawton et al., 1987 Plant Mol. Biol. 9:315-324), the CaMV 35S promoter (Odell et al., 1985 Nature 313:810-812), and the figwort mosaic virus 35S promoter, the light inducible promoter from the small subunit of rubisco, the Adh promoter (Walker et al., 1987 Proc Natl Aca. Sci U.S.A. 84:6624-66280, the sucrose synthase promoter (Yang et al., 1990 Proc. Natl. Acad. Sci. U.S.A. 87:4144-4148), the R gene complex promoter (Chandler et al., 1989. Plant Cell 1:1175-1183), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al. 1982 Cell 29:1015-1026). A plethora of promoters is described in International Patent Application Publication No. WO 00/18963. According to certain currently preferred embodiments, the construct of the present invention comprises the constitutive CaMV 35S promoter or the E8 promoter (Deikman J. et al., Plant Physiol 100:2013-2017)

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3'non-coding sequences is exemplified by Ingelbrecht 1 L et al. (1989. Plant Cell 1:671-680).

In particular embodiments of the present invention, the following elements were used to assemble the DNA constructs of the present invention:

1. A DNA sequence containing a cauliflower mosaic virus (CaMV) 35S promoter plus a CaMV omega translation enhancer upstream the translational initiation ATG codon, containing restriction enzyme sequences, termed 35S:PRO-Ω (Shaul O. and G. Galili, 1993. Plant Mol Biol 23:759-768).
2. A DNA sequence containing E8, an ethylene biosynthesis-related gene which is induced by ethylene and activated to express at the beginning of fruit ripening. Expression of the E8 gene is spatially and temporally regulated in mature tomato fruit (Zhao et al., 2009 J Biosci 34:71-83).
3. A DNA sequence containing the 3' transcription termination and polyadenylation signals from the octopine synthase gene of Agrobacterium tumefacience, termed OCS-TER, with restriction enzyme sequences (Shaul and Galili 1993, supra).

The above described sequences are used as regulatory elements that enable the expression of the encoding nucleic acid sequence within a plant cell.

4. A DNA sequence encoding a pea rbcS3 plastid transit peptide (SEQ ID NO:6), including the necessary restriction enzyme sequences (Shaul and Galili 1993, supra). The encoded peptide, when linked to the AroG DAHPS polypeptide, caused the migration of the later into the plastid.
5. A DNA sequence of the E. coli AroG$_{WT}$ gene (SEQ ID NO:16) which encode the E. coli AroG$_{WT}$ DAHPS enzyme (Having SEQ ID NO:1), or a DNA sequence of a mutated E. coli AroG$_{175}$ (SEQ ID NO:3) encoding the mutated enzyme AroG$_{175}$ DAHPS (SEQ ID NO:2) that is essentially not sensitive to feedback inhibition by phenylalanine or a DNA sequence of a mutated E. coli AroG$_{209}$ (SEQ ID NO:5) encoding the mutated enzyme AroG$_{209}$ DAHPS (SEQ ID NO:4) that is essentially not sensitive to feedback inhibition by phenylalanine.
6. A DNA sequence encoding three copies of a hemagglutinin (HA) epitope tag (SEQ ID NO:7). This epitope allows the detection of the recombinant AroG DAHPS polypeptide by immunoblots with antibodies for the HA epitope tag (Shevtsova et al., 2006. Eur J Neurosci 23:1961-1969).

Those skilled in the art will appreciate that the various components of the nucleic acid sequences and the transformation vectors described in the present invention are operatively linked, so as to result in expression of said nucleic acid or nucleic acid fragment. Techniques for operatively linking the components of the constructs and vectors of the present invention are well known to those skilled in the art. Such techniques include the use of linkers, such as synthetic linkers, for example including one or more restriction enzyme sites.

According to yet another aspect, the present invention provides a method of inducing the synthesis of at least one of shikimate, chorismate and an aromatic amino acid in a plant, comprising (a) transforming a plant cell with an exogenous polynucleotide encoding DAHPS feedback insensitive and (b) regenerating the transformed cell into a transgenic plant comprising at least one cell having an altered content of at least one of shikimate, chorismate and an aromatic acid compared to a corresponding cell of a non transgenic plant.

Methods for transforming a plant cell with nucleic acids sequences according to the present invention are known in the art. As used herein the term "transformation" or "transforming" describes a process by which a foreign DNA, such as a DNA construct, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome, and as such represents a transient trait. According to preferred embodiments the nucleic acid sequence of the present invention is stably transformed into a plant cell.

There are various methods of introducing foreign genes into both monocotyledonous and dicotyledonous plants (for example, Potrykus I. 1991. Annu Rev Plant Physiol Plant Mol Biol 42:205-225; Shimamoto K. et al., 1989. Nature 338:274-276).

The principal methods of the stable integration of exogenous DNA into plant genomic DNA includes two main approaches:

Agrobacterium-mediated gene transfer: The Agrobacterium-mediated system includes the use of plasmid vectors that contain defined DNA segments which integrate into the plant genomic DNA. Methods of inoculation of the plant tissue vary depending upon the plant species and the Agrobacterium delivery system. A widely used approach is the leaf-disc procedure, which can be performed with any tissue explant that provides a good source for initiation of whole-plant differentiation (Horsch et al., 1988. Plant Molecular Biology Manual A5, 1-9, Kluwer Academic Publishers, Dordrecht). A supplementary approach employs the Agrobacterium delivery system in combination with vacuum infiltration. The Agrobacterium system is especially useful in the generation of transgenic dicotyledenous plants.

Direct DNA uptake: There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues.

According to certain embodiments, transformation of the DNA constructs of the present invention into a plant cell is performed using Agrobacterium system.

The transgenic plant is then grown under conditions suitable for the expression of the recombinant DNA construct or constructs. Expression of the recombinant DNA construct or constructs alters the quantity of at least one of shikimate, chorismate and an aromatic acid of the transgenic plant compared to their quantity in a non transgenic plant.

The regeneration, development and cultivation of plants from single plant protoplast transformants or from various transformed explants is well known in the art (Weissbach and Weissbach, In.: Methods for Plant Molecular Biology, (Eds.), 1988 Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

Selection of transgenic plants transformed with a nucleic acid sequence of the present invention as to provide transgenic plants having altered amount of shikimate, chorismate, aromatic amino acids and secondary metabolites derived therefrom is performed employing standard methods of molecular genetic, known to a person of ordinary skill in the art. According to certain embodiments, the nucleic acid sequence further comprises a nucleic acid sequence encoding a product conferring resistance to antibiotic, and thus transgenic plants are selected according to their resistance to the antibiotic. According to other embodiments, the antibiotic serving as a selectable marker is one of the aminoglycoside group consisting of paromomycin and kanamycin. According to additional embodiments, the nucleic acid sequence further comprises a nucleic acid sequence encoding a product conferring resistance to an herbicide, including, but not limited to, resistant to Glufosinate ammonium. According to yet further embodiments, the nucleic acid sequence further comprises a polynucleotide encoding at least one copy of the hemagglutinin (HA) epitope tag, operably linked to the polynucleotide encoding AroG DAHPS. According to certain currently preferred embodiments, the nucleic acid sequence comprises a polynucleotide encoding three copies of the hemagglutinin (HA) epitope. According to these embodiments, proteins are then extracted and transgenic plants are selected according to the protein extracts reacting with HA-epitope antibodies.

Extraction and detection of the metabolites synthesized by the transgenic plant cells can be performed by standard methods as are known to a person skilled in the art. According to certain embodiments, the metabolites of the present invention are extracted and analyzed by GC-MS as described by Mintz-Oron et al., 2008 (Plant Physiol 147(2): 823-51), LC-MS and HPLC as described by Fraser et al. 2000 (Plant J 24(4):551-558) and as described in the Example section hereinbelow.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines, or pollen from plants of these important lines is used to pollinate regenerated plants. A transgenic plant of the present invention containing a desired polypeptide is cultivated using methods well known to one of skill in the art.

There is a variety of methods in the art for the regeneration of plants from plant tissue. The particular method of regeneration will depend on the starting plant tissue and the particular plant species to be regenerated.

Also within the scope of this invention are seeds or plant parts obtained from the transgenic plants. Plant parts include differentiated and undifferentiated tissues, including but not limited to, roots, stems, shoots, leaves, pollen, seeds, tumor tissue, and various forms of cells and culture such as single cells, protoplasts, embryos, and callus tissue. The plant tissue may be in plant or in organ, tissue or cell culture.

The following non-limiting examples hereinbelow describe the means and methods for producing the transgenic plants of the present invention. Unless stated otherwise in the Examples, all recombinant DNA and RNA techniques, as well as horticultural methods, are carried out according to standard protocols as known to a person with an ordinary skill in the art.

EXAMPLES

Materials and Methods
Plasmid Construction and Plant Transformation

The coding DNA sequence of the *E. coli* AroG gene, encoding the DAHPS, was amplified by PCR with the following oligonucleotides: forward 5' CAT GCATGCTGATGAATTATCAGAACGACGA-3' (SEQ ID NO:10) that introduces a SphI restriction site (underlined); and reverse 5'-GGAATTCCCCGCGACGCGCTTTTA-CTG-3' (SEQ ID NO:11) that introduces an EcoRI restriction site (underlined). Two kinds of recombinant genes were constructed: AroGWT (the original sequence), encoding the feedback sensitive enzyme, and $AroG_{175}$, having a point mutation at the 524 bp (leading to the replacement Leu175Glu), encoding the feedback insensitive enzyme. AroG175 was constructed using PCR with the following oligonucleotides: forward 5'-GTGCACCGCGAAC AGGCATCAGGGCTT-3 (SEQ ID NO:12) and reverse 5'-AAGCCCTGATGCCTGTTCGCGGTGCAC-3' (SEQ ID NO:13). The $AroG_{209}$, having a point mutation at the 625-626 bp (leading to the replacement Phe209Ala), encoding the feedback insensitive enzyme. AroG209 was constructed using PCR with the following oligonucleotides: forward 5'-GCGCCGCACTGCGCCCTGTCCGTAACG-3 (SEQ ID NO:14) and reverse 5'-CGTTACGGACAGG GCGCAGTGCGGCGC-3' (SEQ ID NO:15). The RuBisCO small subunit-3A plastid transit peptide (Shaul, O. and G. Galili. Plant Mol Biol, 1993. 23: p. 759-768) was fused in frame to the 5' end of the AroG open reading frame. The AroG 3' was fused to three copies of an HA epitope tag fused to an octopine synthase terminator. The chimeric gene and the vector were digested with the restriction enzymes NotI (BioLab) respectively and combined by T4 DNA ligase (BioLabs) and the entire fragment was sub-cloned into the Ti plasmid pBART, a derivative of pART27 (Gleave, A. P., Plant Mol Biol 1992. 20(6):1203-7). For sequence alignment, the NCBI database was used (http://www.ncbi.nlm.nih.gov). *Agrobacterium* tumefacies (A. tumefacies) strain EHA-105, was transformed with the plasmids by electrophoresis using gene pulser apparatus (Bio Rad).

Wild type (WT) *Arabidopsis thaliana*, ecotype Colombia plants were inoculated by submersing inflorescences in the transformed *A. tumefacies* culture as previously described (Clough, S. J. and A. F. Bent, 1998. Plant J 16(6):735-43).

Wild type tomato, ecotype M82 plants were inoculated by submersing cotyledon in the transformed *A. tumefacies* culture as previously described (McCormic S., Plant Tissue Manual. 1991. B6:109; Fillati, J. J. et al., 1987. Bio/Technology 5:726-730).

Plant Material and Growth Condition

*Arabidopsis* seeds were collected dried, and sowed on soil. Young seedlings were selected for transgenic plants selection by spraying with Basta (Glufosinate ammonium; Bayer CropScience). Tomato seeds sterilized and sowed on Petri dishes containing Nitsch complete medium pH 6 (Duchefa, Haarlem, Netherlands) supplemented with 1% sucrose and 1% plant agar. For transgenic tomato plants selection, 50 µg/ml kanamycine was added to the growth medium. The seeds were imbibed for 48 h at 4° C. and transferred to a climate-controlled growth room with a regime of 16 h light/8 h dark (long day conditions) on 22° C.

T2 generation plants were measured for progeny test and lines with a single gene insertion were selected based on 3:1 genetic segregation. 5MT (Sigma/Aldrich) Trp analog resistance test was performed as previously described (Li J. and R. L. Last, 1996. Plant Physiol 110(1):51-59; Tzin V. et al., 2009. Plant Journal 60(1):156-167).

The resistant seedlings were removed to soil and grown in the greenhouse at 22° C. under long day conditions. For testing the response of plant growth to 5MT (Sigma/Aldrich), plant seeds homozygous for $AroG_{175}$ and control plants were germinated on Nitsch medium as described above supplemented with 75, 100 or 150 µM of 5MT (Li and Last 1996, supra)

Selection of Transformed Lines

Western blot analysis was performed using anti-HA tag antibodies in order to identify the mutated plants which translated the chemeric gene (Stepansky, A. and G. Galili. Plant Physiol, 2003. 133(3): p. 1407-15). Additionally, $T_2$ generation plants were measured for progeny test and lines with a single insertion gene were selected based on 3:1 genetic segregation.

Metabolomics Analysis

*Arabidopsis* Transgenic Lines Samples Preparation

Metabolic analysis was performed with aerial tissues of *Arabidopsis* seedlings (100 mg frozen powder) expressing the $AroG_{WT}$ and $AroG_{175}$ and control lines (n=5-6). For UPLCqTOF-MS analysis, *Arabidopsis* samples were extracted in 450 µl of methanol 80%. Sample preparation and injection conditions were as previously described (Mintz-Oron, S. et al., Plant Physiol, 2008. 147(2):823-51). For GC-MS analysis, the seedlings were harvested, frozen, ground and extracted in 450 µl of methanol, 750 µl methanol, 750 µl water and 375 µl chloroform as previously described (Malitsky, S. et al., Plant Physiol, 2008. 148(4): 2021-2049). To assess whether the different lines in the analysis vary in their composition of metabolites, Student's t-test (JMP software) was performed. The resulting P-values were controlled for multiple hypotheses testing using a 5% FDR cutoff (Hochberg Y. and Y. Benjamini 1990. Statistics in Medicine 9(7):811-818). The PCA plots were generated using the TMEV4 software (Saeed, A. I. et al., Biotechniques, 2003. 34(2):374-378; Scholz, M. et al., 2004. Bioinformatics, 20(15):2447-2454).

Tomato Transgenic Lines Samples Preparation

Non-targeted metabolic analysis was performed with three developing stages of tomato fruits (500 mg frozen powder) expressing the $AroG_{175}$ and $AroG_{209}$ and WT (n=5), extracted in 1.5 ml of methanol 100%. Sample preparation and injection conditions were performed as previously described (Mintz-Oron, S., et al. Plant Physiol, 2008. 147 (2): p. 823-51).

UPLC-qTOF-MS and GC-MS Analyses

The analysis of the raw UPLC-qTOF-MS data was performed using the XCMS software that performs chromatogram alignment, mass signal detection and peak integration (Smith, C. et al., Anal Chem, 2006. 78:779-787) from the Bioconductor package (v. 2.1) for the R statistical language (v. 2.6.1). XCMS was used with the following parameters: fwhm=10.8, step=0.05, steps=4, mzdiff=0.07, snthresh=8, max=1000. Injections of samples in the positive and negative ionization modes were performed in separate injection sets and pre-processing was done for each ionization mode independently. Differential mass ions were determined using a Student's 1-test (JMP software). The GC-MS analysis was performed as previously described (Malitsky, S. et al., Plant Physiol, 2008. 148(4):2021-2049), (n=5-6) The Xcalibur software v.1.4 (Thermo Finnigan; http://www.thermo.com/) was used for data analysis and compounds were identified by comparison of their retention index (R1) and mass spectrum to those generated for authentic standards analyzed on the same instrument. In cases when standards were not available, compounds were putatively identified by comparison of their R1 and mass spectrum to those present in the mass spectra library of Max-Planck-Institute for Plant Physiology, Golm, Germany (Q_MSRI_ID, http://csbdb.mpimp-golm.mpg.de/csbdb/gmd/msri/gmd_msri.html) and the commercial mass spectra library NIST05 (www.nist.gov). The response values for metabolites resulting from the Xcalibur processing method were normalized to the ribitol internal standard. A Student's t-test analysis was done on metabolites level with significant changes in the two transformed $AroG_{175}$ genotypes by using the JMP software. Then, the PCA plots were generated using the TMEV4 software (Saeed et al. 2003, supra; Scholz, et al. 2004, supra).

RNA Extraction and Microarray Analysis

All experiments analyzing RNA expression levels were carried out using two replicates of aerial tissues of 10 days old *Arabidopsis* seedlings from plants grown under controlled environment conditions. Total RNA was extracted as previously described (Chomczynski P., 1993. Biotechniques 15(3):532-537) and treated with DNAase RQ-1 (Promega). RNA was then amplified using 1-cycle Affimetrix labeling using the standard Affymetrix protocol. Hybridization, labeling, scanning and data extraction were performed according to the standard Affymetrix protocols. Transcriptome analysis was carried out using Partek Genome Suite software (www.partek.com). Pre-processing was carried out using the Robust Microarray Averaging (RMA) algorithm (Irizarry R. A. et al., 2003. Biostatistics 4(2):249-264). One way ANOVA analysis was performed, fold change between lines was calculated (two fold) and FDR was applied to correct form multiple comparisons (Hochberg and Benjamini 1990, supra). Over-representation analysis was performed by PageMan tool (http://mapman.mpimp-golm.mpg.de/general/ora/ora.shtml) (Usadel B. et al., 2006. BMC Bioinformatics 7:535). Visualization of metabolic pathways and other functional categories was preformed with the MapMan software tool (Usadel B. et al., 2005. Plant Physiol 138(3):1195-1204.). Common locus number (AGI) was used from TAIR nomenclature (http://www.arabidopsis.org). For a two-step quantitative RT-PCR, a Platinum SYBR SuperMix (Invitrogen) RT-PCRs were tracked on an ABI 7300 instrument (Applied Biosystems). Each sample was amplified by PCR using the same amount of cDNA template in triplicate reactions as previously describe (Mintz-Oron et al. 2008, supra).

Example 1

Figure 2D:
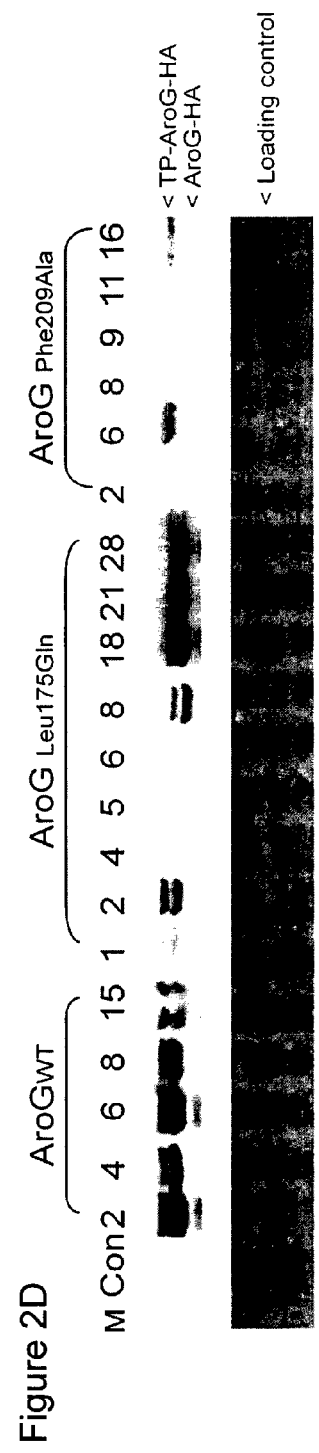
FIG. 2D Shows immunoblot analysis of protein extracts from independently transformed lines reacted with anti HA antibodies. The upper band (TP-AroG-HA) represents the precursor polypeptide, while the lower band (AroG-HA) represents the mature polypeptide. Loading control showed comparable levels of stained proteins in the different lanes.

Generation of Transgenic *Arabidopsis* Plants Expressing a Bacterial Feedback Insensitive Dahps Enzyme and Initial Metabolic Analyses To study the importance of DAHPS in regulating fluxes bridging primary and secondary metabolism in plants, *Arabidopsis* plants were transformed with either a chimeric $AroG_{WT}$ or a chimeric $AroG_{175}$ or $AroG_{209}$ genes (FIG. 2, panels A, B and C respectively) encoding the plastid-targeted WT and feedback-insensitive bacterial DAHPS enzymes, respectively (Hu et al. 2003, supra). Targeting the bacterial enzymes to the plastid, where the Shikimate pathway operates in plants, was obtained by an in-frame fusion of a DNA encoding a plastid transit peptide at the 5' end of the coding DNA sequences of the two chimeric genes. The chimeric genes were also fused in frame at their 3' to a DNA encoding hemagglutinin (HA) epitope tag (FIG. 2 A-C), to allow the detection of the recombinant genes in the transgenic plants. To examine the polypeptides produced by the chimeric AroG transgenes, proteins from independently transformed plants were subjected to immunoblot analysis with anti-HA antibodies. As shown in FIG. 2D, the immunoblot analysis revealed that the transgenic plants expressing the plastidic AroG constructs produced two AroG-derived polypeptide bands: (i) the lower band corresponding in size to the mature bacterial AroG polypeptide (42.5 kD); and (ii) the upper band, corresponding in size to the unprocessed AroG containing the plastid transit peptide (48.1 kD). This indicated that a major portion of the $AroG_{WT}$, $AroG_{175}$ and $AroG_{209}$ polypeptides, produced by these transgenes, were processed to remove the plastid transit peptide and translocated into the plastids. Homozygous T2 plants were generated that contained a single insertion, based on their 3:1 segregation for resistance to Basta selection in the heterozygous state, and those were used for further analysis. The transgenic $AroG_{WT}$ and $AroG_{175}$ expressing plants had comparable phenotypes to the control plants (data not shown) and were fully fertile.

Figure 3:
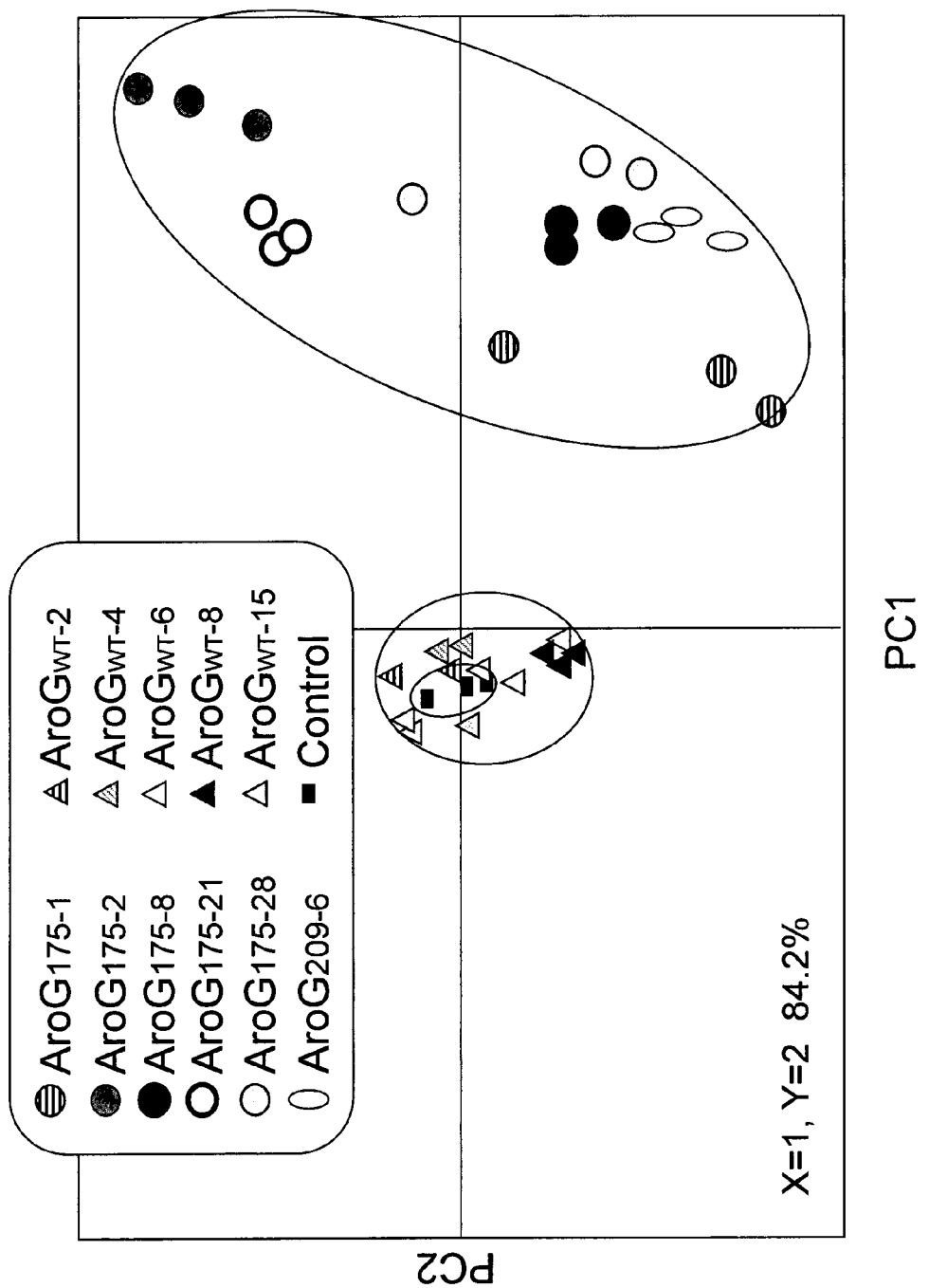
FIG. 3 demonstrates that the metabolic profiles of *Arabidopsis* plants expressing the $AroG_{WT}$, $AroG_{175}$ and $AroG_{209}$ genes are markedly different as compared to the control. Principal Component Analysis (PCA) plot of datasets were obtained from 90 targeted metabolites. Triangles mark plants expressing the $AroG_{WT}$ gene (five lines); circles mark plants expressing the $AroG_{175}$ gene (five lines); ovules mark plants expressing the $AroG_{209}$ gene (one lines); and squares mark the control plants. Each data point represents an independent sample. The combined percentages of the first two dimension variance are given in this panel. The samples were extracted from aerial tissues of 10 days old *Arabidopsis* seedlings.

A global view of the effect of the expression of the $AroG_{WT}$, $AroG_{175}$ and $AroG_{209}$ transgenes on plant metabolism was obtained by performing gas chromatograph-mass spectrometry (GC-MS) analysis of polar compounds of derivatized extracts. 20 days-old plants from four independently transformed plants of each genotypes (2-3 independent analyses from each genotype; each derived from extracts made from ~7 plants) as well as WT plants (five independent analyses) were taken for the analysis. The data set was first analyzed by a Principal Component Analysis (PCA). In this analysis, the metabolic profiles of the control and $AroG_{WT}$ genotypes grouped together, and were completely separated from the $AroG_{175}$ and $AroG_{209}$ genotypes (FIG. 3). Interestingly, there was also some separation among the five $AroG_{175}$ genotypes (FIG. 3), implying an effect of the different levels of $AroG_{175}$ expression in each of these genotypes on the extent of metabolic alteration.

Figure 4:
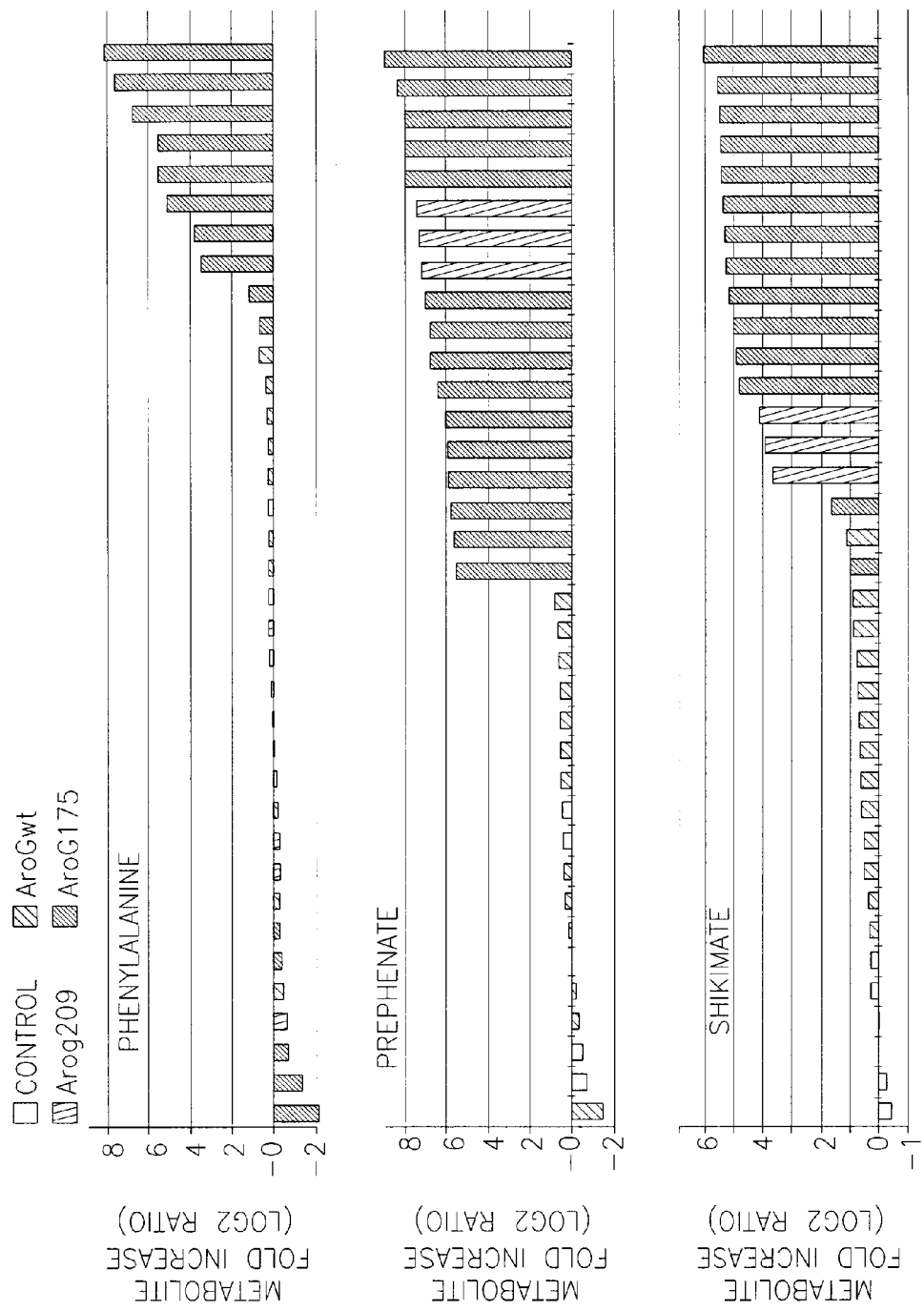
FIG. 4 shows differences in the levels of metabolites in the transgenic plants expressing the $AroG_{WT}$, $AroG_{175}$ and $AroG_{209}$ genes. Each individual histogram represents the relative level of shikimate, prephenate or phenylalanine in a single GC-MS fractionation derived from a single extract (100 mg tissue derived from ten plants of 20 days old *Arabidopsis* leaves). These histograms represent metabolite fold increase derived from independently transformed lines of $AroG_{WT}$ (five lines), $AroG_{175}$ (five lines), $AroG_{209}$ (one lines) with three replicates per genotype and control plants with five replicates. The relative metabolite level in each individual GC-MS analysis was calculated as the pick area of metabolite divided by the pick area of the internal standard Ribitol. Histograms of each genotype are ordered (left to right) in increased relative metabolite level.

To test further whether $AroG_{WT}$, $AroG_{175}$ and $AroG_{209}$ expression alters the levels of metabolites associated with the shikimate and aromatic amino acid biosynthesis pathways (FIG. 1), the mass signals associated with such metabolites that could be detected in the GC-MS (see Material and Methods section) was specifically examined. As shown in FIG. 4, the levels of shikimate, prephenate and phenylalanine (see metabolite locations in FIG. 1) were higher in the different $AroG_{175}$ and $AroG_{209}$ lines, but not in the $AroG_{WT}$ genotypes, compared to the control plants. This suggested that the feedback-insensitivity trait of the $AroG_{175}$ enzyme is essential for enhancement of the flow of primary carbon metabolism via the shikimate pathway into the production of aromatic amino acids. Plants expressing the $AroG_{175}$ polypeptide were therefore further studied.

Example 2

Metabolic Analysis of *Arabidopsis* Plants Expressing the $AroG_{175}$ Gene

The effect of $AroG_{175}$ expression on a wide range of primary and secondary metabolites was examined in two independently transformed homozygous $AroG_{175}$ line, $AroG_{175-2}$ and $AroG_{175-21}$. These lines expressed either medium ($AroG_{175-2}$) or relatively high ($AroG_{175-21}$) level of the $AroG_{175}$ polypeptide (FIG. 2D), and contained a single insertion, based on their 3:1 segregation for antibiotic resistance. Aerial tissues of 10 days old seedlings of these two lines as well as the control genotype were subjected to both GC-MS and targeted and non-targeted liquid chromatography-mass spectroscopy (LC-MS) analyses. PCA plot of the GC-MS data displayed significant separation between the two $AroG_{175}$ genotypes and the control genotype (FIG. 3). Furthermore, PCA of the LC-MS data demonstrated a relatively small separation between the $AroG_{175-2}$ and the control line, while a considerably higher separation between the $AroG_{175-21}$ and both the control and $AroG_{175-2}$ lines (data not shown). Analysis of the levels of specific metabolites by the GC-MS and LC-MS (FIG. 5) also showed that, as expected, the changes in the levels of specific metabolites were principally stronger in the $AroG_{175-21}$ line than the $AroG_{175-2}$ line. GC-MS analysis showed that the levels of five metabolites were significantly increased in the AroG lines including the primary metabolites shikimate, prephenate and phenylalanine (FIG. 5A-C), as well as the secondary metabolites phenylacetonitrile (isothiocyanate) and homogentisate (Tyr-derivative that is a precursor of tocopherols and tocotrienols) (FIG. 5D, E).

In the LC-MS analysis, the $AroG_{175-2}$ line generally displayed milder changes in the levels of the different metabolites compared to the $AroG_{175-21}$ line (data not shown). Thus, the non-targeted LC-MS analysis focused only on metabolites that their level was significantly different between the AroG$_{175-21}$ line and the control, but also showed similar direction of change in the AroG$_{175-2}$ line. The non-targeted LC-MS analysis of AroG$_{175-21}$ line revealed a total of 4473 mass signals, of which the levels of 2414 were significantly altered (up or down regulated) as compared to the control. Assuming an average of five mass signals per single metabolite (Malitsky S. et al., 2008. Plant Physiology 148(4):2021-2049), AroG$_{175}$ expression in the AroG$_{175-21}$ line resulted in altered levels of ~500 metabolites. In regard to the two other aromatic amino acids, this analysis showed that the level of tryptophan was 2.6-fold higher in the AroG$_{175-21}$ line, compared to the control, while its level in the AroG$_{175-2}$ line was not significantly different from the control (FIG. 5F). The level of tyrosine was not altered in these two transgenic lines as compared to the control (data not shown). These results imply that *Arabidopsis* seedlings possess: (i) stronger channeling of chorismate into the Phe/Tyr branch than towards the Trp branch and (ii) stronger channeling of the Phe/Tyr branch towards Phe than towards Tyr biosynthesis (see FIG. 1).

Figure 5A:
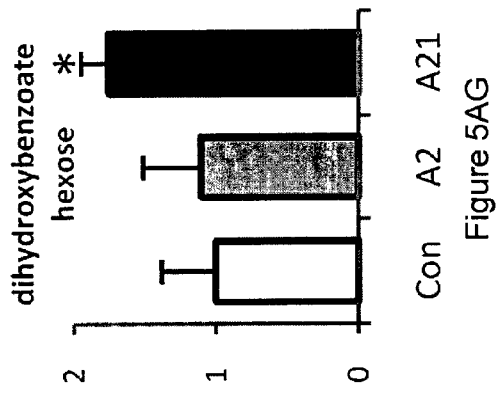
FIG. 5 demonstrates the relative level of metabolites detected by GC-MS and LC-MS in the control and transgenic *Arabidopsis* plants expressing the $AroG_{175}$ gene. The metabolite levels represents the fold change of two $AroG_{175}$ lines ($AroG_{175-2}$, A2 and $AroG_{175-21}$, A21) compared to control (Con) plants (n=5-6). The samples were extracted from aerial tissues of 10 days old *Arabidopsis* seedlings and metabolites were detected by GC-MS (FIG. 5A-FIG. 5E) and LC-MS (FIG. 5F-FIG. 5AL). Bars on the top of the histograms indicate the standard error. Asterisks indicate a statistically significant difference between the two $AroG_{175}$ lines and control genotype using the Student's t-test; with FDR cutoff (P-value<0.05). Abbreviations: Cyanidin*, cyanidin3-O-([2-(6-O-(sinapoyl)-(xylosyl)-6-O-(p-O(glucosyl)-p-coumaroyl-glucoside]-5-O-[6-O (malonyl); Con, control; A2, $AroG_{175-2}$; A21, $AroG_{175-21}$.
Figure 5A:
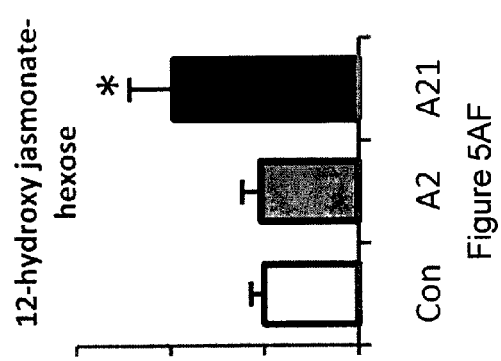
Figure 5A:
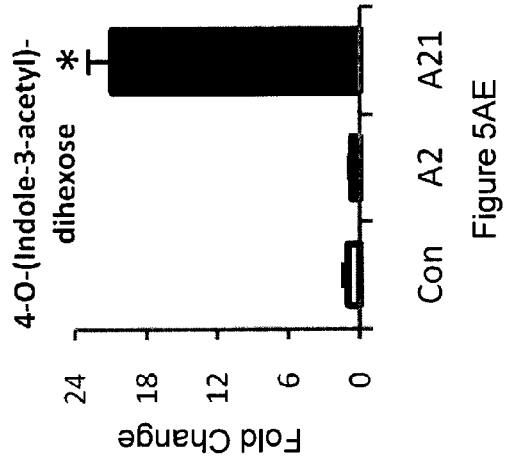
Figure 5A:
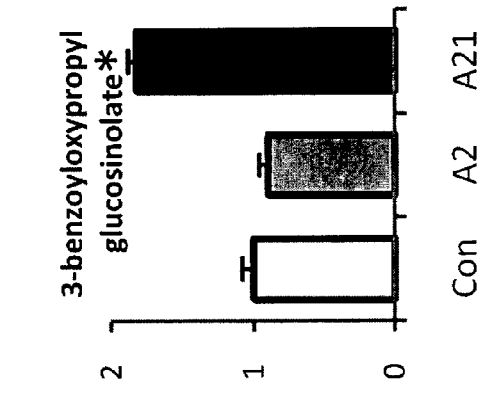
Figure 5A:
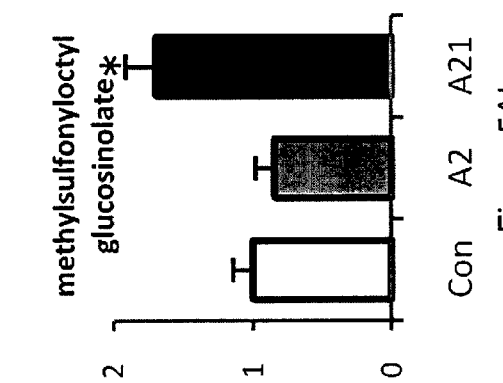
Figure 5A:
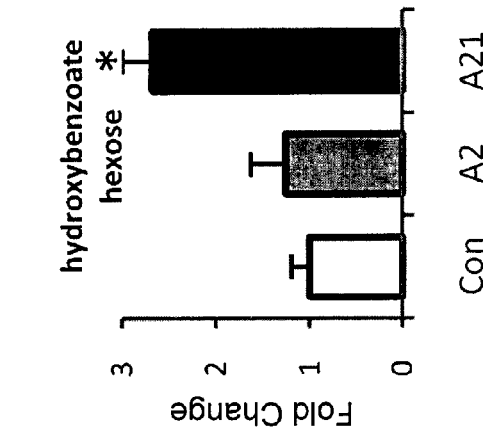
Figure 5A:
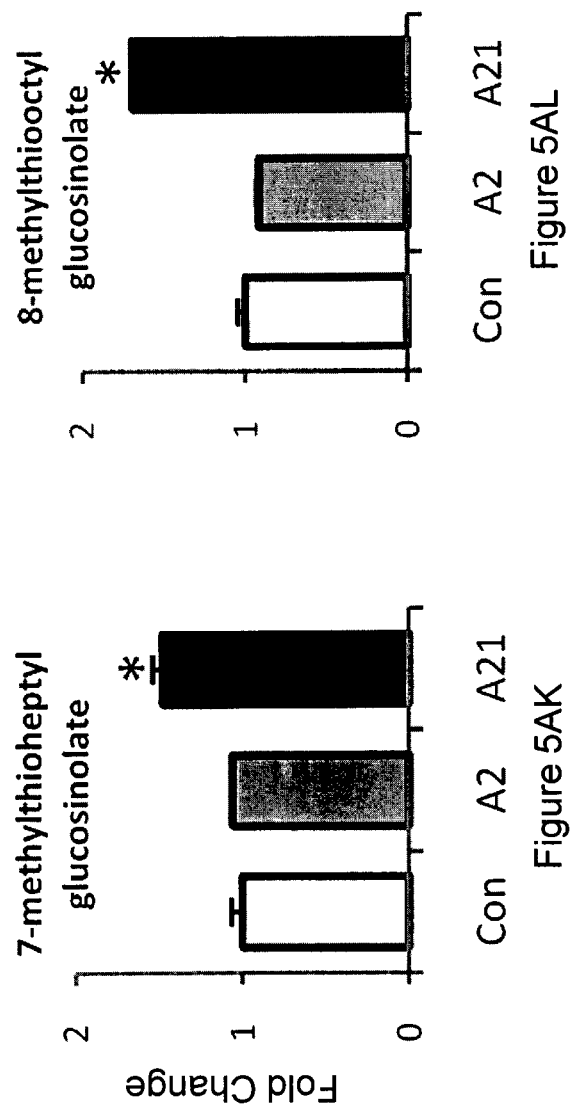

The LC-MS analysis also showed that the level of a number of phenylalanine-derived phenylpropanoids secondary metabolites is significantly higher in AroG$_{175-21}$ compared to the control plants (FIG. 5G-Z). These secondary metabolites include: Phe-3-carboxy-2-hydroxy, coumaratehexose (I-III), ferulate hexose (I-III), a ferulic acid derivative (I-III), sinapoyl hexose, keampferol deoxyhexose-hexose-deoxyhexose, sinapate, coniferin, sinapyl alcohol, sinapoyl malate, kaempferol deoxyhexose-deoxyhexose, kaempferol deoxyhexose, cyanidin 3-O-[2-(2-(sinapoyl)xylosyl)-6-O-(4(glucosyl)-p-coumaroyl)glucoside]5-[6-O-(malonyl)-glucoside and 2-phenylethyl glucosinolate. The level of some secondary metabolites derived from tryptophan were also significantly higher in the AroG$_{175-21}$ line, including the tryptophan-derived glucosinolates 4-hydroxyindolyl-3-methyl glucosinolate, 1-methoxyindole glucosinolate, 1-(1H-indole-3-carboxylate)-glucopyranose, and 4-methoxyindole glucosinolate as well as the IAA conjugate; 4-O-(indole-3-acetyl)-dihexose (FIG. 5AA-AE). Additional metabolites that their levels were higher in the Aro$_{G175-21}$ line include the hormone conjugates jasmonate (12-hydroxy jasmonate-hexose) and salicylate derivatives (dihydroxybenzoate hexose and hydroxybenzoate hexose) as well as the Met-derived glucosinolates: methylsulfonyloctyl glucosinolate, 3-benzoyloxypropyl glucosinolate, 7-methylthioheptyl glucosinolate and 8-methylthiooctyl glucosinolates (FIG. 5AF-AL).

Figure 6:
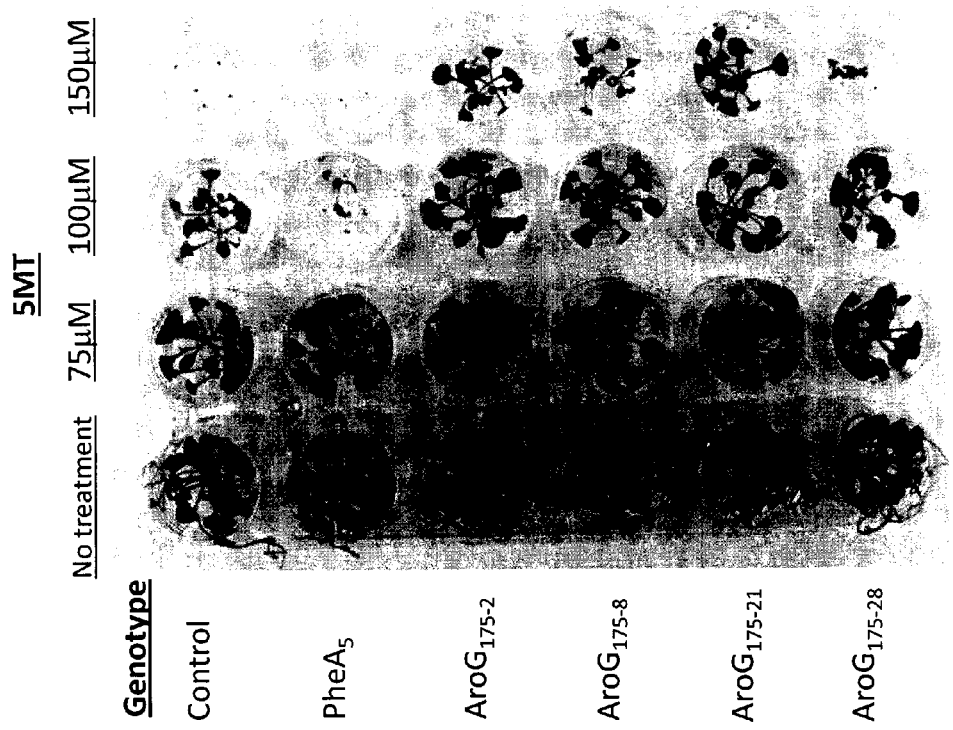
FIG. 6 shows the effect of 5-methyl-Trp (5MT) on the growth of *Arabidopsis* plants expressing the $AroG_{175}$ gene. Seeds were germinated on media containing three concentrations of 5MT: 75, 100, 150 μM and media without treatment. The different genotypes tested are indicated near the location of the seedlings on the plates.

Since tryptophan level was higher in the AroG$_{175-21}$, but not in the AroG$_{175-2}$, as compared to the control lines (FIG. 5F), we decided to indirectly examine whether AroG175 expression also influences the flux from chorismate to tryptophan (FIG. 1). To address this issue we used the tryptophan analog 5-methyl-Trp (5MT) that slows down the rate of tryptophan biosynthesis (Widholm J. M., 1972. Biochimica et Biophysica Acta 279(1): 48-57; Kisaka H. et al., 1996. Breeding Science 46: 221-226). Plants that are resistant to 5MT normally display increased levels of tryptophan. The inventors of the present invention have previously shown that expression of the *E. coli* PheA* gene (encoding a bi-functional feedback-insensitive chorismate mutase/prephenate dehydratase that converts chorismate via prephenate to phenylpyruvate) in *Arabidopsis* renders the plants more sensitive to growth on medium containing 5MT (Tzin V. et al., 2009. Plant J. 60(1):156-67). As shown in FIG. 6, growth of the four AroG$_{175}$ expressing lines on 5MT-containing medium was considerably better than that of the control plants, supporting the analytical data indicating that AroG$_{175}$ expression up regulates tryptophan biosynthesis.

Example 3

Generation of Transgenic Tomato Plants Expressing a Bacterial Feedback Insensitive Dahps Enzyme and Initial Metabolic Analyses To study the importance of DAHPS in regulating fluxes bridging primary and secondary metabolism in plants, tomato plants were transformed with either a chimeric AroG$_{175}$ or AroG$_{209}$ genes (FIG. 2, panels B and C respectively) encoding the insensitive bacterial DAHPS enzymes. Targeting the bacterial enzymes to the plastid, where the Shikimate pathway operates in plants was obtained by an in-frame fusion of a DNA encoding a plastid transit peptide at the 5' end of the coding DNA sequences of the two chimeric genes. The chimeric genes were also fused in frame at their 3' to a DNA encoding hemagglutinin (HA) epitope tag (FIG. 2 B-C). T$_1$ tomato plants were genetically tested for the presence of AroG insertion and kanamycin resistance (data not shown). The transgenic AroG$_{175}$ and AroG$_{209}$ expressing plants had comparable phenotypes to the control plants and were fully fertile (data not shown).

At the first stage of studying the effect of expression of the AroG$_{175}$ and AroG$_{209}$ transgenes on plant metabolism, LC-MS analysis was performed for ripe tomato fruit from five independently transformed genotypes for each transgenic plants (5-6 independent analyses from each genotype; each derived from extracts made from ~10 plants) as well as WT plants (five independent analyses). To get a global view on the metabolic effects of the AroG$_{175}$ and AroG$_{209}$ genotypes, the data set was first analyzed by a PCA plot. In this analysis, the metabolic profile of the control was completely separated from the AroG$_{175}$ and AroG$_{209}$ genotypes (FIG. 8A). Interestingly, there was also some separation among the two AroG$_{175}$ genotypes (AroG$_{175-6}$ and AroG$_{175-11}$) and three AroG$_{209}$ genotypes (AroG$_{209-4}$, AroG$_{209-8}$ and AroG$_{209-9}$) implying an effect of the different expression levels of the feedback-insensitive AroG in each of these genotypes on the extent of metabolic alteration. To test further whether AroG$_{175}$ and AroG$_{209}$ expression alters the levels of the aromatic amino acids, their mass signals were specifically examined. The levels of all three aromatic amino acids were significantly increased in all five genotypes (FIG. 8B). Metabolites accumulated in developing tomato fruit obtained from plants expressing AroG$_{209}$ are presented in Table 1. An increased level of a number of phenylalanine-derived secondary metabolites including anthocyanins, flavonoids, coumarate and caffeoylquinate derivatives as well as monosaccharides and oligosaccharides is shown.

TABLE 1

Accumulation of metabolites in developing tomato fruit obtained from plants expressing AroG$_{209-9}$ gene and in fruit obtained wild-type (WT) tomato plants.

|  |  | Peel | | | Flesh | | |
| --- | --- | --- | --- | --- | --- | --- | --- |
|  | Metabolite | MG | Br | Ripe | MG | Br | Ripe |
| Amino acids | Phe | 1.0 | 4.7 | 89.0 | 0.9 | 2.4 | 22.1 |
|  | Tyr | 1.6 | 2.4 | 171.9 | 0.9 | 2.7 | 15.3 |
|  | Trp | 0.6 | 2.2 | 4.1 | 0.5 | 1.4 | 1.4 |
|  | Asn | 0.4 | 0.5 | 0.5 | 0.6 | 0.9 | 0.5 |
|  | Gln | 0.1 | 0.1 | 0.4 | 0.3 | 0.7 | 0.4 |
|  | Gly | 0.5 | 1.3 | 1.7 | 1.0 | 1.2 | 1.5 |
|  | Ile | 0.7 | 1.2 | 2.2 | 1.0 | 1.1 | 2.0 |
|  | N-acetyl-glutamate | 0.1 | 0.2 | 0.4 | 0.7 | 0.8 | 0.4 |
|  | Thr | 0.5 | 1.0 | 1.1 | 0.7 | 1.0 | 1.2 |
| Organic acid | Fumaric acid | 1.5 | 1.8 | 2.5 | 1.0 | 1.2 | 1.2 |
|  | Prephenic acid | 7.6 | 354.3 | 604.8 | 3.4 | 276.3 | 235.9 |
|  | Shikimic acid | 2.3 | 2.5 | 17.4 | 1.1 | 2.5 | 62.9 |
| Sugars | Cellobiose | 0.9 | 1.3 | 8.0 | 1.0 | 1.2 | 22.0 |
|  | Fructose | 1.7 | 1.0 | 1.0 | 1.2 | 1.0 | 1.1 |
|  | Fructose-6-phosphate | 0.5 | 0.8 | 0.9 | 0.8 | 0.7 | 0.6 |
|  | Maltose | 1.3 | 1.2 | 1.4 | 1.2 | 0.9 | 1.5 |
|  | Mannose | 1.7 | 1.2 | 1.2 | 1.1 | 1.0 | 1.1 |
|  | Raffinose | 1.2 | 2.0 | 103.1 | 0.4 | 2.8 | 92.3 |
|  | Trehalose | 0.5 | 0.7 | 73.6 | 1.8 | 0.9 | 5.3 |
| Polyamine | Putrescine | 1.1 | 0.6 | 0.3 | 0.8 | 0.8 | 0.2 |
| Nucleosides | Guanosine | 0.8 | 0.9 | 1.9 | 1.0 | 0.7 | 1.6 |
| Phenylpropanoids | 3-Caffeoylquinic acid | 0.9 | 1.3 | 2.9 | 1.9 | 1.1 | 2.2 |
|  | 4-Caffeoylquinic acid | 0.7 | 1.0 | 2.1 | 1.3 | 0.8 | 1.4 |
|  | Coumaric acid | 0.7 | 2.7 | 164.8 | 0.4 | 2.6 | 613.6 |
|  | Coumaric acid hexoside or deriv I | N.D | N.D | N.D | 1.1 | 1.8 | 114.5 |
|  | Coumaric acid-hexose I | 0.8 | 0.6 | 15.3 | 0.4 | 0.4 | 1.1 |
|  | Kaempferol-glucose-rhamnose | 1.0 | 0.9 | 0.6 | 1.1 | 0.9 | 108.7 |
|  | Naringenin | 0.9 | 0.4 | 0.6 | 0.5 | 10.1 | 1.8 |
|  | Naringenin chalcone-hexose IV | 0.8 | 0.7 | 5.2 | N.D | N.D | N.D |
|  | Quercetin | 0.4 | 0.7 | 2.6 | 0.2 | 0.7 | 1.1 |
|  | Quercetin-hexose-deoxyhexose-pentose-p-coumaric acid | 1.0 | 1.1 | 3.9 | N.D | N.D | N.D |
|  | Tricaffeoylquinic acid | 0.9 | 0.7 | 2.3 | 0.6 | 1.2 | 2.0 |
| Steroidal Alkaloids | Dehydrolycoperoside G, F, A | 2.8 | 1.1 | 2.6 | 1.5 | 1.5 | 2.9 |
| Cartenoids | Phytoene | N.D | N.D | 0.2 | N.D | N.D | ~0.001 |
|  | Phytofluene | N.D | N.D | 0.1 | N.D | N.D | ~0.001 |
|  | Lycopene like | N.D | N.D | 0.3 | N.D | N.D | 0.55 |

Metabolite levels are shown as fold change ±SE from five (UPLC-qTOF-MS analysis) or six (GC-MS analysis) or four (UPLC) independent samples in comparison with the WT. The metabolite levels are presented as fold change (AroG$_{209-2}$/WT) in each developing stage. The three developing stages are: mature green (MG; ~42 days post anthesis (DPA)), breaker (Br; ~44 DPA) and red (red; ~48 DPA) and separated to peel and flesh. P-values are shown as <0.05 (FDR). Terms in bold indicate a statistically significant increase as analyzed by two-way ANOVA and Student t-test. N.D. not detected.

Example 4

Metabolic Analysis of Tomato Fruits Expressing the AroG$_{209}$ Gene

The effect of AroG$_{209}$ expression of T2 generation on a wide range of primary and secondary metabolites was examined on selected transformed homozygous AroG$_{209-9}$ genotypes. This genotype contained a single insertion, based on PCR and antibiotic resistance. In order to study the effects of AroG$_{209}$ expression on tomato fruit metabolism, tomato fruit in three developing stages were subjected to Lc-MA analysis: mature green (about 42 days post anthesis (DPA); breaker (about 44 DPA); and red (about 48 DPA). 5-6 independent analyses from AroG$_{209}$ and WT genotypes at each developing stages were examined. Each analysis was derived from extracts made from three fruit collected from 10 plants. To get a global view on the metabolic effects of the AroG$_{209}$ expression in tomato peel tissue, a PCA was performed of datasets obtained from 2,725 mass signals in negative ion mode. Interestingly, the mature green stage of both AroG$_{209-9}$ and WT combine, a weak separation occurs in the breaker stage and a completely separation occurs in the red stage (FIG. 9A). PCA plots of metabolic profiles obtained by UPCL-QTOF analysis is presented in FIG. 9B. The most significantly fold change occurred in the red developing stage and the level of unique 1000 mass signals was significantly increased. The level of all three aromatic amino acids was significantly higher in the red stage of AroG$_{209-9}$ genotype, with higher increase in the level of phenylalanine and tyrosine (FIG. 10 and Table 1). The metabolic analysis also showed that increased levels of a number of phenylalanine-derived phenylpropanoids secondary metabolites as well as the tyrosine catabolic product.

Figure 11:
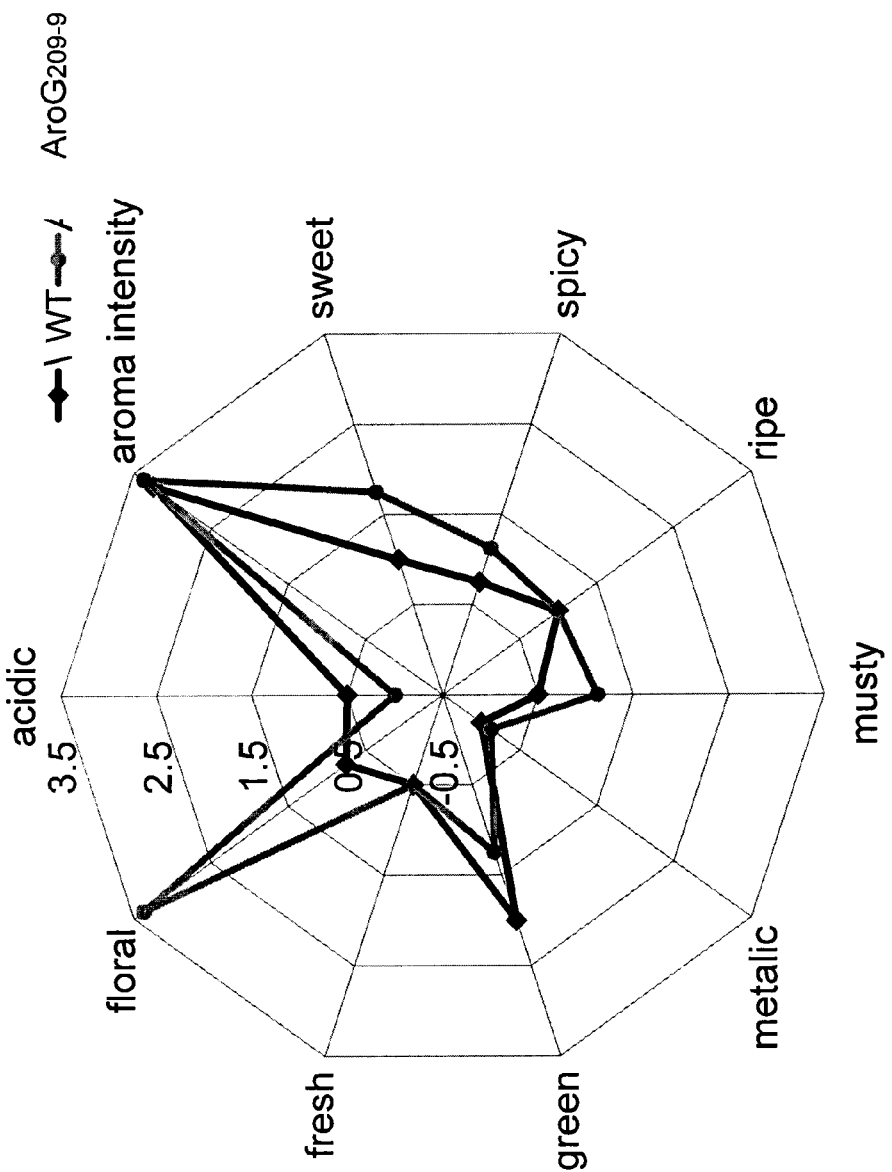
FIG. 11 demonstrated the sensory profile of red ripe tomato fruit obtained from transgenic plants expressing the $AroG_{209-9}$ gene. Each descriptor was scored on a 0-5 point scale.

Organoleptic panel who tested ripe red fruit obtained from AroG$_{209-9}$ expressing plant determined that the fruit possessed better floral flavor (FIG. 11).

Example 5

Effects of AroG$_{175}$ Expression on Gene-Expression Networks

The effect of AroG$_{175}$ expression on the global transcriptome of *Arabidopsis* was studied. A microarray analysis was performed with samples extracted from aerial tissues of 10 days old control and AroG$_{175-2}$ seedlings, using the Affymetrix AtH1 GeneChip. The AroG$_{175-2}$ line that was shown to have a moderate change in the metabolite was selected, to reduce the chance of pleiotropic effects. ANOVA analysis of the microarray results followed multiple hypotheses testing using a 5% FDR cutoff, indicated that expression of a relatively small number of genes (109 genes) showed a significant and at least 2-fold change between the control and AroG$_{175-2}$ line, indicating a relatively moderate effect of AroG expression on the *Arabidopsis* transcriptome.

Genes that were consistently up-regulated (77 genes) and down-regulated (32 genes) were classified by over-representation analysis using the PageMan and MapMan software tools (http://mapman.mpimpgolm.mpg.de/general/ora/ora.shtml; (Usadel et al. 2006, supra). The major effects of the AroG$_{125-2}$ gene included a stimulation of the expression of 37 genes associated with biotic stress (Tables 2 and 3).

TABLE 2

Over represented categories of up-regulated gene (minimum two fold increase)

| BIN (category number) Page Man | Main category | Sub category (1) | Sub category (2) | number of probe sets | P-value (FDR) |
|---|---|---|---|---|---|
| 10 | Cell wall | | | 3 | 1.2E−08 |
| 10.8 | | Pectinesterases | | 2 | 5.4E−06 |
| 12 | Nitrate metabolism | | | 3 | 5.4E−06 |
| 12.1.1 | | Nitrate reductase | | 2 | 5.4E−06 |
| 16 | Secondary metabolism | | | 7 | 2.9E−19 |
| 16.2 | | Phenylpropanoids | | 2 | 5.4E−06 |
| 16.4 | | N misc | | 3 | 1.2E−08 |
| 16.4.1 | | | Alkaloid-like | 3 | 1.2E−08 |
| 17 | Hormone metabolism | | | 4 | 2.8E−11 |
| 17.4 | | Cytokinin | | 2 | 5.4E−06 |
| 17.4.2 | | | Cytokinin-signal transduction | 2 | 5.4E−06 |
| 20 | Stress | | | 10 | 2.7E−27 |
| 20.1 | | Biotic stress | | 9 | 1.3E−24 |
| 21 | Redox regulation | | | 3 | 1.2E−08 |
| 27 | RNA | | | 12 | 1.1E−32 |
| 27.3 | | Regulation of transcription | | 12 | 1.1E−32 |
| 27.3.26 | | | MYB - transcription factor family | 2 | 5.4E−06 |
| 27.3.3 | | | AP2/EREBP, APETALA2/ Ethylene-responsive element binding protein family | 2 | 5.4E−06 |
| 27.3.5 | | | ARR - transcription factor family | 2 | 5.4E−06 |
| 27.3.7 | | | C2C2(Zn) Constans-like zinc finger family (circadian clock) | 2 | 5.4E−06 |
| 29 | Protein | | | 2 | 5.4E−06 |
| 29.4 | | postranslational modification | | 2 | 5.4E−06 |
| 30 | Signalling | | | 7 | 2.9E−19 |
| 30.2 | | Receptor kinases | | 3 | 1.2E−08 |
| 30.3 | | Calcium | | 4 | 2.8E−11 |
| 33 | Development | | | 3 | 1.2E−08 |
| 34 | Transport | | | 5 | 6.2E−14 |

TABLE 3

Over represented categories of down-regulated gene (minimum two fold decrease)

| BIN (category number) Page Man | Main category | Sub category (1) | Sub category (2) | number of probsets | P-value (FDR) |
|---|---|---|---|---|---|
| 11 | Lipid metabolism | | | 2 | 9.2E−07 |
| 27.3 | RNA | Regulation of transcription | | 8 | 3.1E−25 |
| 27.3.66 | | | Psudo ARR transcription factor family | 2 | 9.2E−07 |
| 27.3.7 | | | C2C2(Zn) Constans-like zinc finger family (circadian clock) | 3 | 8.4E−10 |
| 29 | Protein | | | 2 | 9.2E−07 |
| 29.5 | | Protein degradation | | 2 | 9.2E−07 |

The biotic stress category included genes associated with hormone metabolism (cytokinin, absicisic acid, salicylate and jasmonate), transcription factors (MYBs, WRKYs and APETALA2/Ethylene-responsive element binding proteins), signaling (calcium and cytokinin AAR-genes), pathogenesis (PR proteins), disease resistance (TIR-NB proteins), transporters and redox regulation. In addition, genes that putatively encode proteins associated with secondary metabolism were induced, including phenylprpanoid metabolism, Met-aliphatic-glucosinolates and a gene associated with Trp-derived indole-glucosinoltes. Another enriched category displaying increased expression was associated with nitrate assimilation. Notably, the expression level of 16 genes, categorized as genes associated with the circadian clock, was also induced in the $AroG_{175-2}$ transcriptome. These circadian clock-related genes included those encoding MYB transcription factors, Zinc Finger B-box type proteins with a CCT DNA-binding domain and three other genes, encoding proteins associated with the circadian clock cascade including TOC1, Pseudo-response regulator and ELF4 (Early flowering 4). To corroborate the microarray results, a quantitative RT-PCR analysis was also performed on a representative sample of genes whose mRNA level was higher in the $AroG_{175-2}$ than in the control line in the microarray analysis. This analysis, which was performed on both $AroG_{175-2}$ and $AroG_{175-21}$ lines, confirmed the gene expression results obtained by the microarray analysis.

Example 6

Aromatic Profile of Fruit from $AroG_{209-9}$ Expressing Tomato Plants

A panel of 10 expert trained flavorists evaluated the aroma of fruit samples obtained from tomato plants expressing the $AroG_{209-9}$ gene. Preliminary tests were carried out to improve the ability of the assessors to recognize odour defects and consistently quantify sensory properties. The panelists had previously been trained in the quantitative description of tomato attributes according to selection trials based on French norms (ISO8586-1, AFNOR V09-003). For each fruit sample, flavorists evaluated whole fruits for peel profiling and cut fruits—for the evaluation of flesh. Aroma evaluation was carried out by sniffing the samples by all panel members. Several attributes were chosen: acidic floral, fresh, green, metallic musty, ripe, spicy, and sweet in addition to global aroma intensity. Scores values were between 0 (none) to 5 (very strong). When completed, panel members discussed their scores and agreed on the final summarizing score of each aroma group. The results are summarized in FIG. 11, showing that several aroma attributes are more significant in the fruit obtained from the transgenic plant compared to fruit of wild type tomato plants.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A transgenic dicot plant comprising at least one plant cell comprising an exogenous polynucleotide encoding *E. Coli* AroG 3-deoxy-d-arabino-heptulosonate-7-phosphate synthase (DAHPS) having the amino acid sequence set forth in SEQ ID NO: 2 or SEQ ID NO: 4 and having at least a 7-fold increase in phenylalanine or prephenate as compared to the level of said phenylalanine or of said prephenate in a transgenic dicot plant expressing wild type *E. coli* AroG DAHPS set forth by SEQ ID NO:1, or as compared to a wild type control dicot plant of the same type.

2. The transgenic dicot plant of claim 1, wherein the polynucleotide encoding SEQ ID NO:2 comprises the nucleic acid sequence set forth in SEQ ID NO:3.

3. The transgenic dicot plant of claim 1, wherein the polynucleotide encoding SEQ ID NO:4 comprises the nucleic acid sequence set forth in SEQ ID NO:5.

4. A plant seed produced by the transgenic dicot plant of claim 1, wherein the seed is used for breeding a transgenic dicot plant having increased levels of phenylalanine or prephenate as compared to the level of said phenylalanine or of said prephenate in a transgenic dicot plant expressing wild type *E. coli* AroG DAHPS or as compared to a wild type control dicot plant —of the same type.

5. A tissue culture comprising at least one transgenic cell of the dicot plant of claim 1 or a protoplast derived therefrom, wherein the tissue culture regenerates a transgenic dicot plant having at least a 7-fold increase in phenylalanine or prephenate as compared to the level of said phenylalanine or of said prephenate in a transgenic dicot plant expressing wild type *E. coli* AroG DAHPS or as compared to a wild type control dicot plant of the same type.

6. A method of modifying a flavor of fruit of a dicot plant, comprising (a) transforming a dicot plant cell with an exogenous polynucleotide encoding *E. Coli* AroG DAHPS having the amino acid sequence set forth in SEQ ID NO:4, and (b) regenerating the transformed cell into a transgenic dicot plant, wherein the transformed dicot plant has at least a 7-fold increase in phenylalanine or prephenate as compared to the level of said phenylalanine or of said prephenate in a transgenic dicot plant expressing wild type *E. coli* AroG DAHPS set forth by SEQ ID NO:1, or as compared to a wild type control dicot plant of the same type, and wherein said amino acid sequence modifies a flavor of a fruit as compared to said flavor of said fruit of a wild type control dicot plant of the same type.

7. The method of claim 6, wherein the polynucleotide encoding SEQ ID NO:4 comprises the nucleic acid sequence set forth in SEQ ID NO:5.

8. A method of growing a transgenic dicot plant having a increased levels of -phenylalanine or prephenate, the method comprising growing a seed of the transgenic dicot plant of claim 1, thereby growing the transgenic dicot plant.

9. The method of claim 6, wherein said dicot plant is a crop plant.

10. A transgenic dicot crop plant comprising at least one plant cell comprising an exogenous polynucleotide encoding *E. Coli* AroG 3-deoxy-d-arabino-heptulosonate-7-phosphate synthase (DAHPS) having the amino acid sequence set forth in SEQ ID NO: 4, wherein the transformed dicot crop plant has at least a 7-fold increase in phenylalanine or prephenate as compared to the level of said phenylalanine or of said prephenate in a transgenic dicot crop plant expressing wild type *E. coli* AroG DAHPS set forth by SEQ ID NO:1, or as compared to a wild type control dicot crop plant of the same type, and wherein said amino acid sequence modifies a flavor of a fruit as compared to said flavor of said fruit of a wild type control dicot crop plant of the same type.

11. The method of claim 1, wherein said amino acid sequence set forth by SEQ ID NO: 2 or 4 increases the level of phenylalanine by at least 7-fold in the transgenic dicot plant as compared to the level of said phenylalanine in a transgenic dicot plant of the same type expressing wild type *E. coli* AroG DAHPS.

12. A method of increasing production of a benzeniod phenylpropanoid volatile compound in a crop plant, comprising:
(a) transforming a dicot plant cell with an exogenous polynucleotide encoding *E. Coli* AroG DAHPS having the amino acid sequence set forth in SEQ ID NO: 2 or SEQ ID NO: 4 wherein said amino acid sequence set forth in SEQ ID NO: 2 or SEQ ID NO:4 increases production of said benzeniod phenylpropanoid volatile compound as compared to said production of said benzeniod phenylpropanoid volatile compound in a wild type control dicot plant of the same type, and
(b) regenerating the transformed cell into a transgenic crop plant;
wherein the transgenic dicot crop plant has at least a 7-fold increase in phenylalanine or prephenate as compared to the level of said phenylalanine or of said prephenate in a transgenic dicot crop plant expressing wild type *E. coli* AroG DAHPS set forth by SEQ ID NO: 1, or as compared to a wild type control dicot crop plant of the same type.

13. The method of claim 12, wherein said increased production of said benzeniod phenylpropanoid volatile compound is in a fruit or a flower of said crop plant.

* * * * *